US007632235B1

(12) United States Patent
Karicherla et al.

(10) Patent No.: US 7,632,235 B1
(45) Date of Patent: *Dec. 15, 2009

(54) SYSTEM AND METHOD FOR MEASURING CARDIAC OUTPUT VIA THERMAL DILUTION USING AN IMPLANTABLE MEDICAL DEVICE WITH AN EXTERNAL ULTRASOUND POWER DELIVERY SYSTEM

(75) Inventors: Annapurna Karicherla, Valencia, CA (US); Xiaoyi Min, Thousand Oaks, CA (US); Peter Boileau, Valencia, CA (US); Jong Gill, Valencia, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 639 days.

This patent is subject to a terminal disclaimer.

(21) Appl. No.: 11/099,888

(22) Filed: Apr. 5, 2005

Related U.S. Application Data

(63) Continuation-in-part of application No. 11/066,894, filed on Feb. 25, 2005.

(60) Provisional application No. 60/630,830, filed on Nov. 22, 2004.

(51) Int. Cl.
*A61B 5/029* (2006.01)
*A61B 5/028* (2006.01)
*A61B 8/06* (2006.01)

(52) U.S. Cl. .................. 600/526; 600/454; 600/549

(58) Field of Classification Search ......... 600/437–439, 600/454–459, 462, 466–468, 481, 486, 504–507, 600/510, 526, 300–301, 549, 483; 607/17–26; 128/905; 604/48, 65–67, 500, 506–510
See application file for complete search history.

(56) References Cited

U.S. PATENT DOCUMENTS 4,236,527 A * 12/1980 Newbower et al. .......... 600/505

(Continued)

FOREIGN PATENT DOCUMENTS

EP 0 597 881 B1 12/1992

(Continued)

OTHER PUBLICATIONS

Bell, D., "From Securing Stealth to Ensuring Health: Making Ultrasound Treatment Ultra-Safe", *Ingenia*, Issue 19, May/Jun. 2004, pp. 25-29.

(Continued)

*Primary Examiner*—Carl H Layno
*Assistant Examiner*—Jessica Reidel

(57) ABSTRACT

The implantable device is capable of performing thermal dilution analysis of the cardiac output of a patient using power delivered from an external source. By using power from an external source, the implantable device conserves its power resources for other purposes, such as for pacing or defibrillation therapy. In one example, an external programmer or bedside monitor provides power through a hand-held power delivery wand via electromagnetic induction, with the power routed from a subcutaneous coil to a heating element implanted in the right atrium, which heats blood as it passes through the right atrium. In another example, the heating element is formed of a material that generates heat in response to a beam of ultrasound provided by the wand. In either case, a downstream blood temperature profile is detected using a thermistor implanted in the pulmonary artery and cardiac output is then estimated by analyzing the temperature profile.

18 Claims, 17 Drawing Sheets

U.S. PATENT DOCUMENTS

| | | | | |
|---|---|---|---|---|
| 4,507,974 | A | | 4/1985 | Yelderman ............... 73/861.06 |
| 4,576,182 | A | | 3/1986 | Normann .................... 128/692 |
| 4,809,697 | A | | 3/1989 | Causey, III et al. ...... 128/419 PT |
| 4,819,655 | A | | 4/1989 | Webler ........................ 128/713 |
| 4,858,614 | A | * | 8/1989 | Stevens et al. .............. 600/543 |
| 5,174,299 | A | | 12/1992 | Nelson ........................ 128/692 |
| 5,217,019 | A | | 6/1993 | Hughes ....................... 128/668 |
| 5,285,796 | A | | 2/1994 | Hughes ....................... 128/668 |
| 5,305,760 | A | * | 4/1994 | McKown et al. ............ 600/505 |
| 5,328,460 | A | | 7/1994 | Lord et al. .................... 604/67 |
| 5,394,875 | A | | 3/1995 | Lewis et al. ............ 128/660.09 |
| 5,411,537 | A | | 5/1995 | Munshi et al. ................ 607/33 |
| 5,598,847 | A | * | 2/1997 | Renger ........................ 600/504 |
| 5,682,899 | A | | 11/1997 | Nashef et al. ............... 128/692 |
| 5,687,733 | A | * | 11/1997 | McKown ..................... 600/505 |
| 5,702,431 | A | | 12/1997 | Wang et al. ................... 607/61 |
| 5,733,313 | A | | 3/1998 | Barreras, Sr. et al. ......... 607/33 |
| 5,954,659 | A | * | 9/1999 | Curley et al. ................ 600/505 |
| 5,991,665 | A | | 11/1999 | Wang et al. ................... 607/61 |
| 6,015,387 | A | * | 1/2000 | Schwartz et al. ............ 600/504 |
| 6,277,078 | B1 | | 8/2001 | Porat et al. .................. 600/486 |
| 6,314,323 | B1 | | 11/2001 | Ekwall ......................... 607/23 |
| 6,361,554 | B1 | * | 3/2002 | Brisken ........................ 623/1.1 |
| 6,371,923 | B1 | * | 4/2002 | Roteliuk et al. ............. 600/526 |
| 6,376,968 | B1 | | 4/2002 | Taylor et al. ................. 310/339 |
| 6,400,990 | B1 | | 6/2002 | Silvian ......................... 607/60 |
| 6,438,408 | B1 | | 8/2002 | Mulligan et al. ............ 600/510 |
| 6,496,732 | B1 | | 12/2002 | Wallace |
| 6,505,077 | B1 | | 1/2003 | Kast et al. ..................... 607/61 |
| 6,512,952 | B2 | | 1/2003 | Stahmann et al. .............. 607/9 |
| 6,524,333 | B1 | * | 2/2003 | Claren et al. ................ 623/1.11 |
| 6,572,557 | B2 | | 6/2003 | Tchou et al. ................. 600/483 |
| 6,580,946 | B2 | | 6/2003 | Struble ......................... 607/23 |
| 6,622,045 | B2 | | 9/2003 | Snell et al. .................... 607/30 |
| 6,628,988 | B2 | | 9/2003 | Kramer et al. .................. 607/9 |
| 6,643,546 | B2 | | 11/2003 | Mathis et al. ................... 607/9 |
| 6,645,143 | B2 | | 11/2003 | VanTassel et al. ........... 600/300 |
| 6,645,153 | B2 | | 11/2003 | Kroll et al. .................. 600/481 |
| 6,666,826 | B2 | | 12/2003 | Salo et al. ................... 600/485 |
| 6,709,400 | B1 | * | 3/2004 | Rantala ....................... 600/526 |
| 6,736,782 | B2 | | 5/2004 | Pfeiffer et al. |
| 6,975,903 | B1 | | 12/2005 | Min et al. |
| 2002/0120200 | A1 | | 8/2002 | Brockway et al. ........... 600/488 |
| 2002/0188213 | A1 | * | 12/2002 | Bardy .......................... 600/509 |
| 2002/0193785 | A1 | * | 12/2002 | Naghavi et al. ................ 606/28 |
| 2002/0198459 | A1 | * | 12/2002 | Franco et al. ............... 600/504 |
| 2003/0018255 | A1 | | 1/2003 | Martin et al. ................ 600/437 |
| 2003/0087802 | A1 | | 5/2003 | Urry .............................. 514/2 |
| 2003/0149380 | A1 | | 8/2003 | Fujimoto et al. ............... 601/2 |
| 2003/0216721 | A1 | | 11/2003 | Diederich et al. ............. 606/28 |
| 2004/0181158 | A1 | | 9/2004 | Bowman |
| 2005/0166683 | A1 | | 8/2005 | Krivitski et al. |
| 2005/0240110 | A1 | * | 10/2005 | Liu et al. ..................... 600/505 |
| 2005/0277839 | A1 | * | 12/2005 | Alderman et al. ........... 600/504 |

FOREIGN PATENT DOCUMENTS

| | | |
|---|---|---|
| EP | 0 597 881 B2 | 12/1992 |
| EP | 0 618 780 B1 | 7/1993 |
| EP | 0 955 008 A1 | 11/1999 |
| EP | 1 050 265 A2 | 11/2000 |
| EP | 1 050 265 A3 | 11/2000 |
| WO | WO 91/17703 | 11/1991 |
| WO | WO 99/15075 | 4/1999 |
| WO | WO 01/28419 A2 | 4/2001 |
| WO | WO 01/28419 A3 | 4/2001 |
| WO | WO 2005/000091 A2 | 1/2005 |

OTHER PUBLICATIONS

Gentry, Kenneth L. et al., "*Integrated Catheter for 3-D Intracardiac Echocardiography and Ultrasound Ablation*" IEEE Transactions on Ultrasonics, Ferroelectrics, and Frequency Control, vol. 51, No. 7, Jul. 2004, pp. 799-807.

Kuecherer, Helmut F., et al., "Evaluation of aortic compliance in humans," Am J Physiol Heart Circ Physiol. 2000; 278:H1411-H1413.

NonFinal Office Action, mailed Mar. 17, 2008: Parent U.S. Appl. No. 11/066,894.

NonFinal Office Action, mailed May 28, 2008: Parent U.S. Appl. No. 11/066,894.

Final Office Action, mailed Dec. 31, 2008—Related U.S. Appl. No. 11/066,894.

Advisory Action, mailed Apr. 10, 2009—Related U.S. Appl. No. 11/066,894.

NonFinal Office Action, mailed Apr. 28, 2009—Related U.S. Appl. No. 11/286,114.

NonFinal Office Action, mailed Dec. 16, 2008—Related U.S Appl. No. 11/267,665.

\* cited by examiner

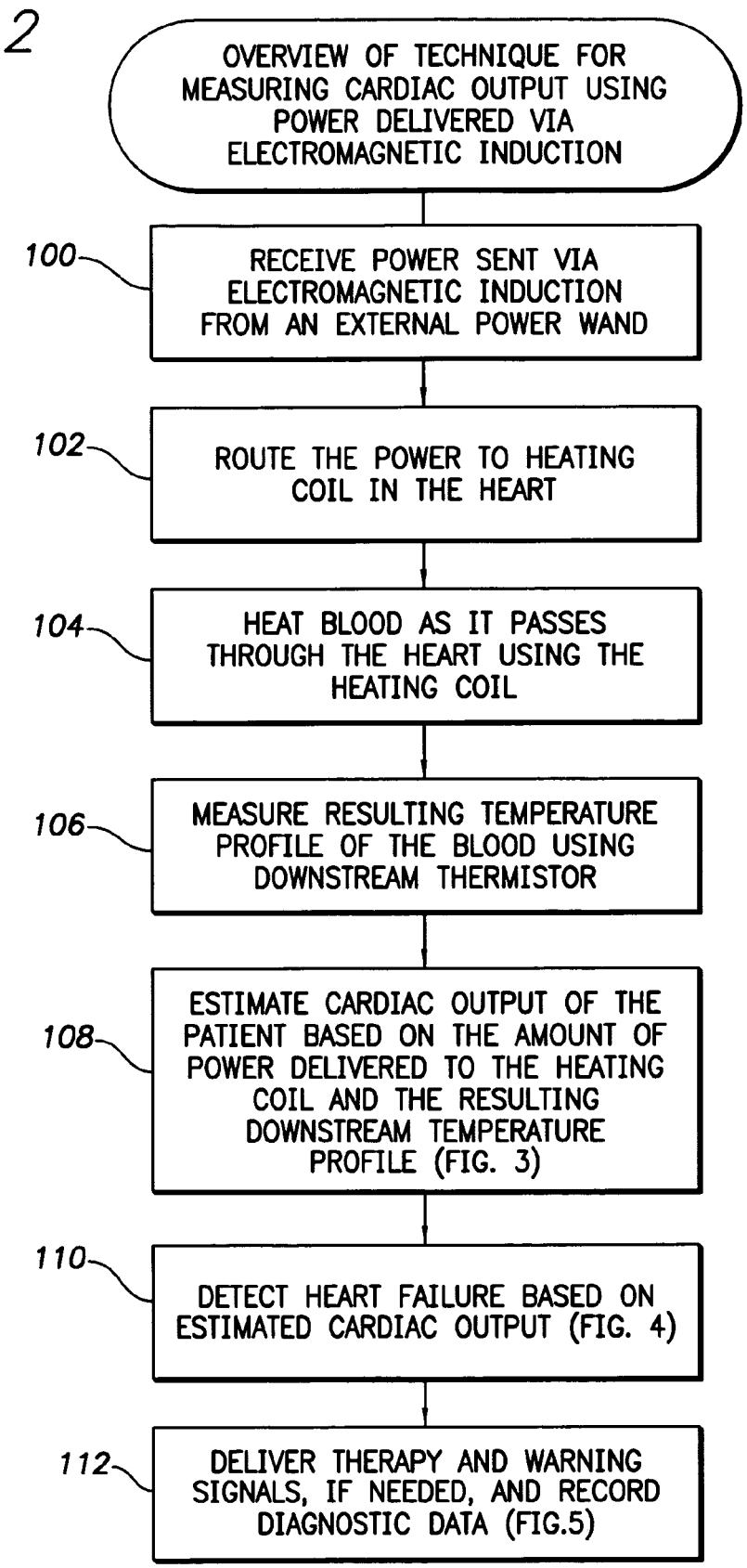

ESTIMATION OF CARDIAC OUTPUT $$CO = \frac{\int_0^{T_{end}} POWER_{in} \, dt}{C_{Pblood} \cdot P_{blood} \int_0^{T_{end}} \{T_{blood}(t) - TO_{blood}\} \, dt}$$

WHERE $C_{Pblood}$ = 0.86 to 0.89 cal /(g · °C)

$P_{blood}$ = 1.052 to 1.064 cm$^3$ / g

CO = cardiac ouput in ml / sec $T_{blood}(t)$ = blood temperature as a function of time $T_{end}$ = the end time $TO_{blood}$ = blood temperature at t = 0 sec $POWER_{in}$ = Electrical Power from blood heater in cal / sec

RETURN TO FIG. 2

FIG. 3

SYSTEM AND METHOD FOR MEASURING CARDIAC OUTPUT VIA THERMAL DILUTION USING AN IMPLANTABLE MEDICAL DEVICE WITH AN EXTERNAL ULTRASOUND POWER DELIVERY SYSTEM

CROSS-REFERENCE TO RELATED APPLICATIONS

This application is a continuation-in-part (CIP) of copending U.S. patent application Ser. No. 11/066,894, filed Feb. 25, 2005, entitled "System and Method for Measuring Cardiac Output Using an Implantable Medical Device," which claims the benefit of U.S. Provisional Application No. 60/630,830, filed Nov. 24, 2004.

FIELD OF THE INVENTION

The invention generally relates to implantable medical devices, such as pacemakers or implantable cardioverter-defibrillators (ICDs), and in particular to techniques for measuring cardiac output via thermal dilution within a patient in which a medical device is implanted.

BACKGROUND OF THE INVENTION

Heart failure is a debilitating disease in which abnormal function of the heart leads can result in blood flow that is insufficient to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles (particularly the left ventricle) to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output. A particularly severe form of heart failure is congestive heart failure (CHF) wherein the weak pumping of the heart leads to build-up of fluids (i.e. congestives) in the lungs and other organs and tissues.

Heart failure has been classified by the New York Heart Association (NYHA) into four classes of progressively worsening symptoms and diminished exercise capacity. Class I corresponds to no limitation wherein ordinary physical activity does not cause undue fatigue, shortness of breath, or palpitation. Class II corresponds to slight limitation of physical activity wherein such patients are comfortable at rest, but wherein ordinary physical activity results in fatigue, shortness of breath, palpitations or angina. Class III corresponds to a marked limitation of physical activity wherein, although patients are comfortable at rest, even less than ordinary activity will lead to symptoms. Class IV corresponds to inability to carry on any physical activity without discomfort, wherein symptoms of heart failure are present even at rest and where increased discomfort is experienced with any physical activity.

The current standard treatment for heart failure is typically centered on medical treatment using angiotensin converting enzyme (ACE) inhibitors, diuretics, beta-blockade, and digitalis. Cardiac resynchronization therapy (CRT) may also be employed, if a bi-ventricular pacing device is implanted. Briefly, CRT seeks to normalize asynchronous cardiac electrical activation and resultant asynchronous contractions associated with CHF by delivering synchronized pacing stimulus to both ventricles. The stimulus is synchronized so as to improve overall cardiac function. This may have the additional beneficial effect of reducing the susceptibility to life-threatening tachyarrhythmias. CRT and related therapies are discussed in, for example, U.S. Pat. No. 6,643,546 to Mathis et al., entitled "Multi-Electrode Apparatus and Method for Treatment of Congestive Heart Failure"; U.S. Pat. No. 6,628,988 to Kramer et al., entitled "Apparatus and Method for Reversal of Myocardial Remodeling With Electrical Stimulation"; and U.S. Pat. No. 6,512,952 to Stahmann et al., entitled "Method and Apparatus for Maintaining Synchronized Pacing."

In view of the potential severity of heart failure, it is highly desirable to detect its onset within a patient and to track its progression so that appropriate therapy can be provided. Many patients suffering heart failure already have pacemakers or ICDs implanted therein or are candidates for such devices. Accordingly, it is desirable to provide such devices with the capability to automatically detect and track heart failure. Heretofore, a number of attempts have been made to provide for monitoring of physiological parameters associated with heart failure using implantable cardiac devices in conjunction with physiological sensors. End diastolic pressure (EDP) has been found to be indicative of heart failure and various techniques have been developed for detecting heart failure based on EDP or related pressure parameters. See, for example, U.S. Pat. No. 6,438,408 to Mulligan et al., entitled "Implantable Medical Device for Monitoring Congestive Heart Failure"; U.S. Pat. No. 6,277,078 to Porat et al., entitled "System and method for monitoring a parameter associated with the performance of a heart"; U.S. Pat. No. 6,666,826 to Salo et al., entitled "Method and Apparatus for Measuring Left Ventricular Pressure"; U.S. Pat. No. 6,580,946 to Struble, entitled "Pressure-Modulated Rate-Responsive Cardiac Pacing"; and U.S. Patent Application 2002/0120200 of Brockway et al., entitled "Devices, Systems and Methods For Endocardial Pressure Measurement."

However, it can be difficult to reliably measure EDP using an implanted system. Moreover, heart failure can begin to occur without a change in EDP. Indeed, severe cardiac depression can occur in the presence of "normal" blood pressures. Accordingly, alternatives to pressure-based heart failure detection techniques have been proposed. In particular, measurements of cardiac output have been found to be effective in detecting and tracking heart failure, as cardiac output usually decreases with heart failure. See, for example, U.S. Pat. No. 6,314,323 to Ekwall, entitled "Heart Stimulator Determining Cardiac Output, by Measuring The Systolic Pressure, for Controlling The Stimulation" and U.S. Pat. No. 6,572,557 to Tchou et al., entitled "System and Method for Monitoring Progression of Cardiac Disease State Using Physiologic Sensors." Cardiac output measurements are particularly advantageous since they can be used as an indicator of acute decompensation before such decompensation is reflected in blood pressure elevation, and hence can provide an early warning of the onset of heart failure.

One promising technique for monitoring cardiac output is thermal dilution wherein a portion of blood passing through the heart is heated and the resulting blood temperature profile is detected downstream using a thermistor. The downstream temperature profile is then evaluated to estimate cardiac output based on conservation of energy principles. See, for example, U.S. Pat. No. 5,174,299 to Nelson entitled "Thermocouple-Based Blood Flow Sensor"; U.S. Pat. No. 5,217,019 to Hughes, entitled "Apparatus and Method for Continuously Monitoring Cardiac Output"; U.S. Pat. No. 5,285,796 also to Hughes, entitled "Method for Continuously Monitoring Cardiac Output"; and U.S. Pat. No. 5,682,899 to Nashef et al., entitled "Apparatus and Method for Continuous Cardiac Output Monitoring."

Heretofore, however, thermal dilution techniques for measuring cardiac output are not practical given current technology. A significant problem with thermal dilution techniques is that a considerable amount of energy is required to heat the blood, thus depleting the energy reserves of the implanted device, which are preferably reserved for delivering defibrillation shocks or the like.

Accordingly, it would be highly desirable to provide improved techniques for use by an implantable device for detecting cardiac output via thermal dilution, which do not consume significant energy resources of the implanted device. It is also desirable to provide techniques for detecting and tracking heart failure based on cardiac output detected using the improved thermal dilution techniques. These and other objectives were achieved by the invention set forth in the parent application. Briefly, an implantable device was described that is capable of performing thermal dilution analysis of the cardiac output of a patient using power delivered from an external source. By using power from an external source, the implantable device conserves its own power resources for other purposes, such as for delivering pacing or defibrillation therapy. In one example, an external programmer or bedside monitor provides power via a hand-held power delivery wand. The wand is placed over the chest of the patient in the vicinity of a subcutaneous power reception coil and power is transferred thereto using electromagnetic induction. The power is then routed to a heating coil implanted in the right atrium, which heats blood as it passes through the right atrium. A resulting downstream blood temperature profile is detected using a thermistor implanted in the pulmonary artery. The cardiac output of the patient is then estimated by analyzing the temperature profile. The techniques of the parent application are also described herein below.

Although the invention of the parent application is effective, room for improvement remains. In particular, it would be desirable to provide for delivery of power from an external source directly to the heating element of the right atrium, so as to eliminate the need for a separate power reception coil and circuitry for relaying power from the receiving coil to the heating coil. It would also be desirable to eliminate the need for transmission of power via electromagnetic induction since electromagnetic induction signals can potentially interfere with the operation of other electronic devices, such as those commonly found in hospitals, clinics and the like. It is to these ends that the invention of the present application is primarily directed.

SUMMARY

In accordance with one embodiment, an implantable system is provided for use within a patient wherein ultrasound provided by an external system is employed to directly heat an implantable heating element. In one example, the implantable system includes a heating element capable of generating heat in response to ultrasound, with the heating element configured for implant in proximity to blood being pumped within the patient for use in heating a quantity of blood in response to ultrasound generated by a source external to the patient. The heating element may be formed, for example, of RP-6401 polyurethane. The system also includes a blood temperature sensor configured for implant downstream from the heating element for detecting a temperature profile of blood heated by the heating element for use, for example, in thermal dilution-based measurements of cardiac output. A cardiac output detection system may also be provided, which is operative to estimate cardiac output based on the blood temperature profile.

The use of ultrasound to directly heat the heating element eliminates the need for a separate implantable power reception coil as may be required with an electromagnetic induction-based power delivery system and also eliminates the need for circuitry for routing power from the reception coil to the heating element, while nevertheless still conserving power sources of the implanted system itself, which may be a pacemaker, ICD or similar device. An ultrasound transducer may be provided in connection with the heating element for measuring the amount of power received via ultrasound by the heating element.

In one exemplary embodiment, the external system is an external programmer or bedside monitor that generates a beam of ultrasound via a hand-held power delivery wand. The wand generates ultrasound at a frequency suitable for directly heating the material from which the implantable heating element is formed. The wand is placed over the chest of the patient near the heating element, which is preferably implanted in the right atrium. The heating element heats up in response to the ultrasound, thus heating blood as it passes through the right atrium. A resulting downstream temperature profile of the blood is detected using a thermistor implanted in the pulmonary artery. The cardiac output of the patient is then estimated based on the amount of power delivered to the heating coil and the resulting temperature profile measured in the pulmonary artery by performing the following calculation:

$$CO = \frac{\int_0^{\tau_{end}} \text{Power}_{in} dt}{c_{Pblood} \cdot P_{blood} \int_0^{\tau_{end}} \{T_{blood}(t) - To_{blood}\} dt}$$

where $\text{Power}_{in}$ is the power delivered to the heating element, $To_{blood}$ is the blood temperature at an initial point in time, $T_{blood}(t)$ is the resulting temperature profile as a function of time, $c_{Pblood}$ is the heat capacity of blood, and $\rho_{blood}$ is the density of blood.

In one specific example, the calculation is performed by microprocessor components in the implanted device based on temperature profile signals received from the thermistor (i.e. based on signals representative of $T_{blood}(t)$). In another example, the calculation is instead performed by the external programmer or bedside monitor based on temperature profile signals received from the implanted device via the hand-held wand, which is also provided with appropriate telemetry circuitry. In either case, changes in cardiac output over time are preferably tracked so as to detect the onset of heart failure, track its progression and to determine its severity. For example, heart failure may be detected if cardiac output falls below a predetermined threshold. Any subsequent progression of heart failure may be monitored by tracking further decreases in cardiac output. Appropriate warning signals are displayed using the external programmer or bedside monitor. Therapies provided by the implanted device may be initiated or adjusted in response to the detection of heart failure. In one example, CRT is activated or optimized upon detection of the onset of heart failure. If an implantable drug pump is provided, appropriate medications may be automatically delivered to the patient to address heart failure.

Thus, various techniques are provided for use with implantable device for detecting cardiac output based thermal dilution via ultrasonic heating of an implanted heating element. The principles of the invention however are also potentially applicable in any circumstance where there is a need to heat selected tissues of the body. To this end, the invention generally comprises an ultrasound generator positioned external to a patient for use with a heating element implanted within the patient that is capable of generating heat in response to ultrasound.

BRIEF DESCRIPTION OF THE DRAWINGS

The above and further features, advantages and benefits of the invention will be apparent upon consideration of the present description taken in conjunction with the accompanying drawings, in which:

FIG. 2 is a flowchart providing an overview of a method for detecting cardiac output via thermal dilution for use by the system of FIG. 1;

FIG. 3 is a flowchart providing an overview of a thermal dilution-based technique for estimating cardiac output for use with the method of FIG. 2;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout. With reference to FIGS. 1-10, systems and methods for delivering power to an implantable system via electromagnetic induction for use in thermodilution analysis will be described. Then, with reference to FIGS. 11-17, systems and methods for delivering power to an implantable system via ultrasound for use in thermodilution analysis will be described.

Overview of Implantable System Using Electromagnetic Induction

Figure 1:
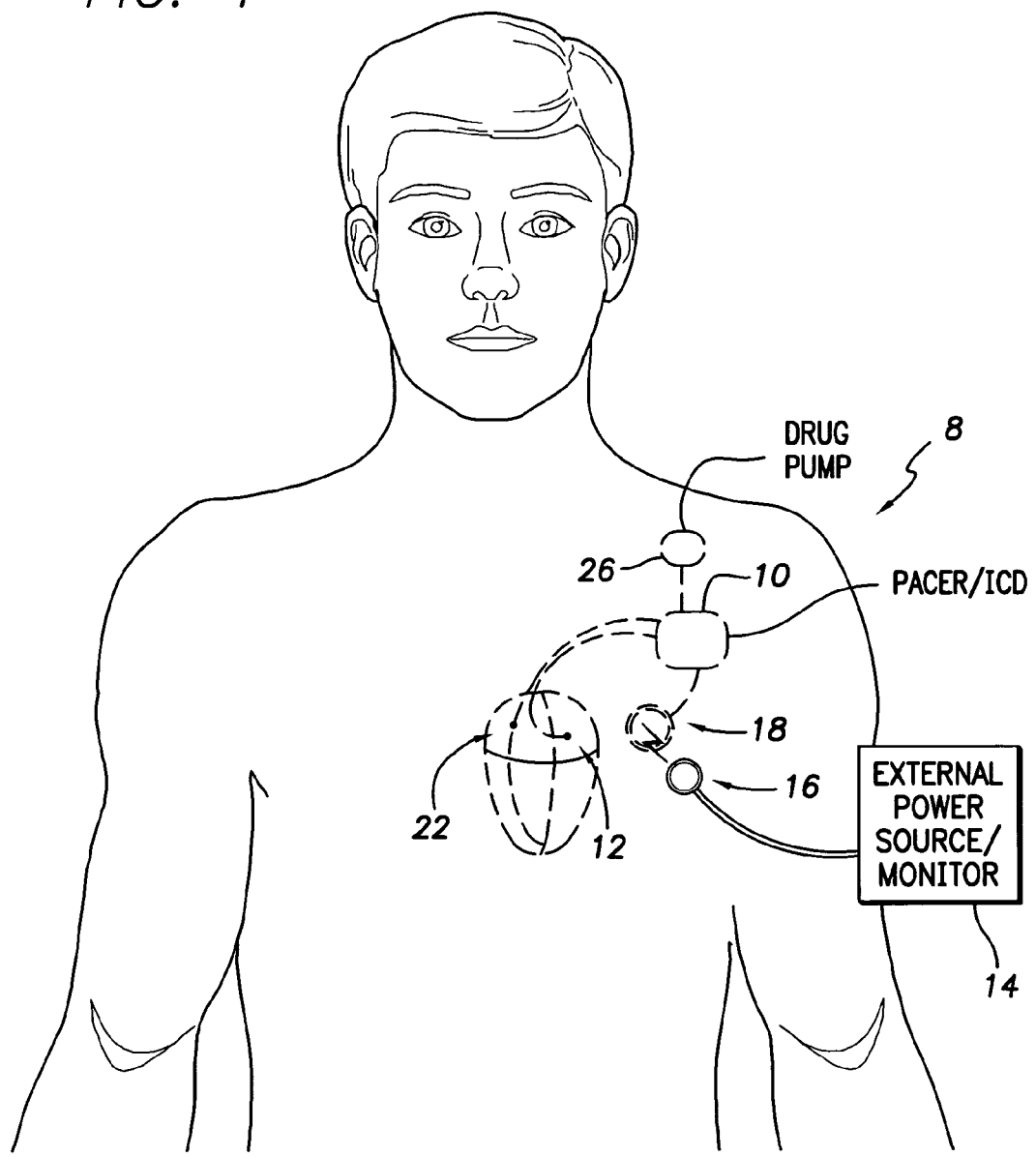
FIG. 1 illustrates pertinent components of a first embodiment of an implantable medical system having a pacemaker or ICD capable of detecting and evaluating heart failure based on thermal dilution cardiac output measurements using power provided via electromagnetic induction from an external source.

FIG. 1 illustrates an implantable medical system 8 capable of estimating cardiac output via thermal dilution techniques using power delivered via electromagnetic induction from an external source. In the preferred implementation, the system is further capable of detecting heart failure based on changes in cardiac output, evaluating its severity, tracking its progression and delivering appropriate therapy.

Implantable medical system 8 includes a pacer/ICD 10 or other cardiac stimulation device that incorporates internal components (shown individually in FIG. 9) for estimating cardiac output based on a thermal dilution blood temperature profile received from a thermistor or other temperature sensor 12 implanted in the pulmonary artery. Briefly, power for performing thermal dilution analysis is provided by an external power source/monitor 14, which may be an external device programmer, bedside monitor or stand-alone power source. The power (initially derived from an AC wall socket) is routed to a power delivery wand 16, which is manually held near the chest of the patient above the implanted pacer/ICD by a physician, nurse or other medical professional or potentially by the patient. Hand-held wand 16 generates high frequency oscillating electromagnetic fields, which in turn induce electrical currents within a subcutaneous power reception coil 18 via electromagnetic induction. In this manner, the power reception coil receives a portion of the power generated by the power delivery wand.

Power received by the reception coil is routed through the pacer/ICD then to a heating coil 22 positioned within the right atrium causing the heating coil to heat up, thus heating a portion of blood passing through the right atrium. The heated blood is pumped by the right atrium into the right ventricle, which then pumps the blood out of the heart through the pulmonary artery past thermistor 12. The thermistor senses a resulting thermal dilution temperature profile, i.e. it senses changes in the temperature of the blood caused by the heating coil. The shape and amplitude of the temperature profile provides an indication of cardiac output. Briefly, if cardiac output is strong, the blood heated by the heating coil will be promptly pumped past the thermistor, thus yielding a pronounced, but short-term, increase in blood temperature at the location of the thermistor. However, if cardiac output is poor, the blood heated by the heating coil will be more slowly pumped past the thermistor, thus yielding a longer but less pronounced increase in blood temperature at the location of the thermistor. Signals representative of the thermal dilution profile are routed from the thermistor to pacer/ICD 10, which estimates cardiac output based upon the thermal dilution profile or forwards the thermal dilution profile data to external power source/monitor 14 for estimation of cardiac output therein. Exemplary techniques for estimating cardiac output based upon a thermal dilution temperature profile are described below, particularly with reference to FIG. 3.

Figure 8:
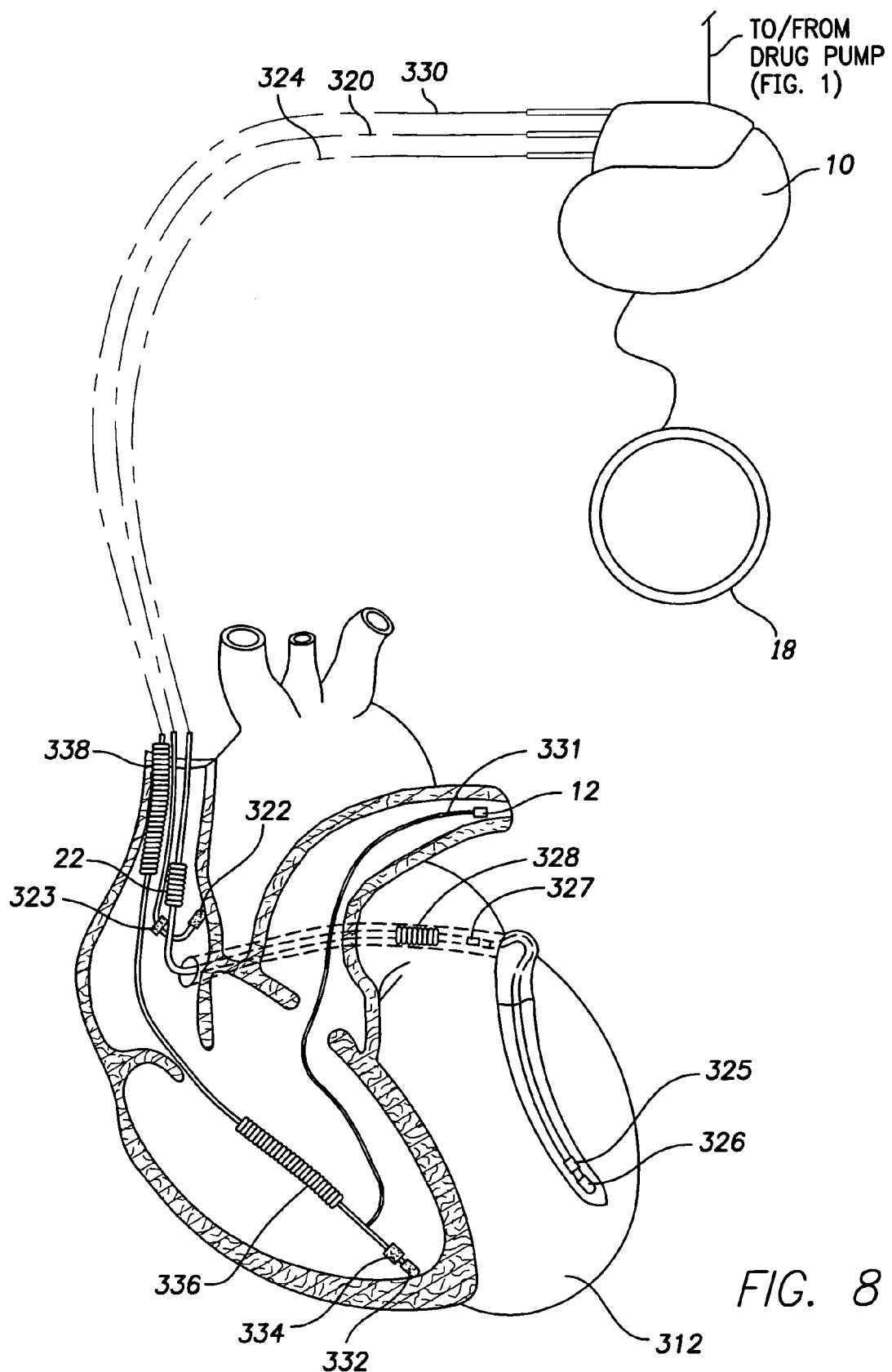
FIG. 8 is a simplified, partly cutaway view, illustrating the pacer/ICD of FIG. 1 along with at full set of leads implanted into the heart of the patient and also illustrating power reception components and thermal dilution-based cardiac output detection components.

Thus, power provided by an external power source is used to heat blood for the purposes of the thermal dilution analysis of cardiac output so that the power resources of the pacer/ICD itself may be conserved for other uses, such as delivering pacing therapy or cardioversion shocks to the patient via the leads implanted in the heart. Note that only a pair of exemplary leads is shown within FIG. 1; a full set of leads and electrodes is illustrated in FIG. 8. Once the cardiac output of the patient has been estimated via thermal dilution analysis, the resulting cardiac output values are then used to detect and evaluate heart failure, if any, within the patient so that appropriate warning signals may be generated and/or appropriate therapy may be automatically initiated. In this regard, if heart failure is initially detected (or if a significant progression of heart failure is detected), warning signals are displayed via the external system 14. In this manner, the physician or other medical professional operating the system is thereby immediately warned. In one example, the external power source is provided as a component of a bedside monitor for use within a hospital, nursing home or the like, thereby allowing physicians, nurses or other medical professionals to easily evaluate the cardiac output of any patients having the appropriate implanted components so that heart failure may be detected and evaluated. In another example, the external power source is provided as a component of an external device programmer for use by a cardiologist during a pacer/ICD programming session, thereby allowing the cardiologist to evaluate cardiac output within the patient following initial device implant or during a follow-up session with the patient. The physician can then program the pacer/ICD so as to take into account the cardiac output of the heart of the patient. Alternatively, the external power source may be provided as a component of a bedside monitor for use in the home of the patient, thereby allowing the patient to initiate a cardiac output analysis as needed, perhaps on a weekly basis, subject to the instructions of his or her physician so that heart failure may be promptly detected and tracked.

If so equipped, the pacer/ICD may automatically adjust therapy delivered to the patient such as by activating CRT upon detection of heart failure or by increasing the aggressiveness of CRT in view of an increase in severity of heart failure. Additionally, or in the alternative, the implantable system may be equipped with a drug pump 26 capable of the delivering drug therapy in an attempt to address heart failure. Discussions of possible medications for use in heart failure patients are provided below. Drug dosages provided by an implantable drug pump may be titrated based on the severity of heart failure. Additionally, the pacer/ICD is capable of performing a wide variety of otherwise conventional pacing and/or defibrillation functions, such as delivering pacing is response to an arrhythmia or generating and delivering defibrillation shocks in response to fibrillation.

Hence, FIG. 1 provides an overview of an implantable system capable of estimating cardiac output via thermal dilution analysis based upon power received from an external source and further capable of detecting and evaluating heart failure and delivering appropriate warnings and therapy. Embodiments may be implemented that do not necessarily perform all of these functions. Rather, embodiments may be implemented that provide, for example, only for estimation of cardiac output but not detection of heart failure based upon cardiac output. In addition, systems provided in accordance with the invention need not include all the components shown in FIG. 1. In many cases, for example, no drug pump is implanted. No attempt is made herein to describe all possible combinations of components that may be provided in accordance with the general principles of the invention. Implanted components of the system of FIG. 1 are shown in phantom lines so as to be clearly distinguished from the external components of the system. The particular shape, size and location of the implanted components shown in FIG. 1 are merely illustrative and may not necessarily correspond to actual implant locations. Preferred implant locations for the leads are more precisely illustrated in FIG. 9.

Thermal Dilution Analysis Using Externally Supplied Power

FIGS. 2-5 summarize the detection of cardiac output and heart failure using thermal dilution analysis, which may be performed by the system of FIG. 1. Beginning at step 100, the receive coil of the implantable system receives power sent via electromagnetic induction from the external power source using a high frequency sinusoidal signal. Preferably, between 5 and 15 watts of power are generated in the receiving coil by the wand. Techniques for transmitting power via electromagnetic induction are set forth in the following patents: U.S. Pat. No. 5,991,665 to Wang et al. entitled "Self-Cooling Transcutaneous Energy Transfer System for Battery Powered Implantable Device"; U.S. Pat. No. 5,702,431 also to Wang et al., entitled "Enhanced Transcutaneous Recharging System for Battery Powered Implantable Medical Device"; and U.S.

Pat. No. 5,411,537 to Munshi, et al., entitled "Rechargeable Biomedical Battery Powered Devices With Recharging And Control System Therefor."

At step 102, the power received by the reception coil is routed to the heating coil implanted within the right atrium. Heating coils for use with thermal dilution analysis are discussed in the aforementioned patents to Hughes and Nashef and in U.S. Pat. No. 4,576,182 to Normann, entitled "Method and Apparatus for Measuring Liquid Flow." Preferably, about 10 watts of power is delivered to the heating coil. The amount of power delivered to the heating coil is less than the amount of power generated by the wand due to power coupling inefficiencies. The pacer/ICD regulates the power delivered to the heating coil to prevent any unduly large amount of power from being delivered, which might damage patient tissue. Otherwise, conventional power regulation circuitry and techniques may be employed. Power regulation techniques for use in implantable medical devices are discussed in: U.S. Pat. No. 6,400,990 to Silvian, entitled "Patient Activated Telemetry Control Unit Using Bidirectional Asymmetric Dual-Mode Telemetry Link To Communicate With An Implanted Device" and within U.S. Pat. No. 4,809,697, to Causey, III et al., "Interactive Programming and Diagnostic System for Use With Implantable Pacemaker."

Note that internal body temperature can vary by about 0.1 C, primarily as a result of respiration. Accordingly, it is preferred that power be delivered to the heating coil in a manner that is uncorrelated with respiration so that respiratory influences can be cancelled out. One technique that may be exploited is to deliver power intermittently in accordance with a binary maximal length sequence. See, for example, Yelderman, U.S. Pat. No. 4,507,974, entitled "Method and Apparatus for Measuring Flow." The binary maximal length sequences constitute pseudo-random noise and thus are not correlated with respiration. A duty cycle is preferably set to about 50%, i.e. power is, on the average, delivered to the heating coil 50% of the time during an overall power delivery interval. The power regulation circuitry of the pacer/ICD may be configured to control power delivery in accordance with the binary sequence during that interval and in accordance with a selected duty cycle. Patient respiration may also be tracked, using otherwise conventional techniques, to aid in ensuring that the power delivered to the coil is uncorrelated with respiration.

Various alternative techniques for detecting heart failure are set forth in: U.S. Pat. No. 7,272,443, of Min et al., entitled "System and Method for Predicting a Heart Condition Based on Impedance Values Using An Implantable Medical Device," filed Dec. 15, 2004, which is a continuation-in-part of U.S. patent application Ser. No. 10/810,437 (pending), of Bornzin et al., entitled "System and Method for Evaluating Heart Failure Based on Ventricular End-Diastolic Volume Using an Implantable Medical Device," filed Mar. 26, 2004 and U.S. Pat. No. 7,139,609, of Min et al., entitled "System and Method for Monitoring Cardiac Function via Cardiac Sounds Using an Implantable Cardiac Stimulation Device."

At step 110, heart failure, if occurring within the patient, is then detected and its progression tracked based on the estimated cardiac output using, for example, the technique illustrated in FIG. 4, which will be described below. The detection of heart failure based on cardiac output may be supplemented by other heart failure detection techniques, such as those based on EDP. At step 112, therapy, if needed, is delivered to the patient. Also at step 112, appropriate warning signals are generated and diagnostic data is recorded. Therapy, warning signals and diagnostic data will be described below with reference to FIG. 5.

Note that steps 100-106 of FIG. 2 are performed by the implanted system. Steps 108-112 may be performed, depending upon the particular implementation, by (1) the implanted system based on data it receives from the thermistor; (2) the external system based on data transmitted from the implanted system; or (3) both. An exemplary technique wherein the implanted device estimates cardiac output and detects heart failure and then transmits that information to the external system is summarized below with reference to FIG. 6. An exemplary technique wherein the external system estimates cardiac output and detects heart failure based on thermal dilution profile data transmitted from the implanted system is summarized below with reference to FIG. 7. Internal components of exemplary implantable systems and external systems are described below with reference to FIGS. 8-10.

Turning now to FIG. 3, an exemplary technique for estimating cardiac output for use at step 108 of FIG. 2 will be described. The technique utilizes the power delivered to the heating coil (in calories per second), which is represented by $Power_{in}$, in combination with the thermal dilution profile sensed by the thermistor, which is represented by $T_{blood}(t)$. Various predetermined parameters are also used including: $c_{Pblood}$, which represents the heat capacity of blood, and $\rho_{blood}$, which represents the density of blood.

At step 114, the cardiac output (CO) is calculated as follows:

$$CO = \frac{\int_0^{T_{end}} Power_{in} dt}{c_{Pblood} \cdot P_{blood} \int_0^{T_{end}} \{T_{blood}(t) - To_{blood}\} dt}$$

where
$c_{Pblood}$=0.86 to 0.89 cal/(g·° C.)
$\rho_{blood}$=1.052 to 1.064 g/cm$^3$
CO=cardiac output in ml/sec
$T_{blood}(t)$=blood temperature as a function of time
$T_{end}$=the end time
$To_{blood}$=blood temperature at t=0 sec
$Power_{in}$=Electrical Power from blood heater in cal/sec This equation assumes that there is little or no heat loss to cardiac tissue and the vasculature when heated blood moves from the right atrium to the pulmonary artery. Also note that, in this equation, $Power_{in}$ is a constant. Hence, this equation is appropriate so long as power is delivered continuously to the heating coil at a constant rate during a power delivery interval beginning at t=0 and ending at $T_{end}$. For any implementation where the delivered power changes with time during that interval (such if power is delivered in accordance with a pseudorandom code so as to be uncorrelated with respiration), then $Power_{in}(t)$ is instead used. See, for example, the Yelderman patent cited above. Although an integral equation is described herein for use in calculating cardiac output based on continuous input functions, those skilled in the art may readily convert the integral equation to a corresponding discrete sum equation for use in programming digital microprocessor components to perform the calculation.

Preferably, $Power_{in}$ is directly measured or regulated by the implanted system using power measurement components of the power regulation circuitry of the pacer/ICD. This allows $Power_{in}$ to be calculated or controlled during each thermal dilution analysis session to account for possible variations in (1) the amount of power actually generated by the wand; (2) the distance between the wand and the implanted receiving coil; and (3) the orientation of the wand relative to the receiving coil during the time in which power is delivered.

Time=0 is the point in time at which power is first delivered to the heating coil, which is also the point in time at which the thermistor starts to measure blood temperature. $T_{end}$ is the point in time at which power is no longer delivered to the heating coil, which is also the point in time at which the thermistor stops measuring the blood temperature. $T_{end}$ is preferably in the range of 15 to 60 seconds.

The calculation of step 114 is performed, depending upon the implementation, by a microprocessor of the pacer/ICD or by a microprocessor of the external system based on data transferred to it from the pacer/ICD via otherwise conventional telemetry techniques. In either case, any needed parameters, such as the density of blood, are preprogrammed values stored in memory. If desired, two or more separate thermal dilution measurements may be made for the same patient—separated by intervals of time sufficient to allow the blood and heating coil to return to body temperature—with the cardiac output values then averaged together. In any case, once the cardiac output is calculated, processing returns to FIG. 2.

Figure 4:
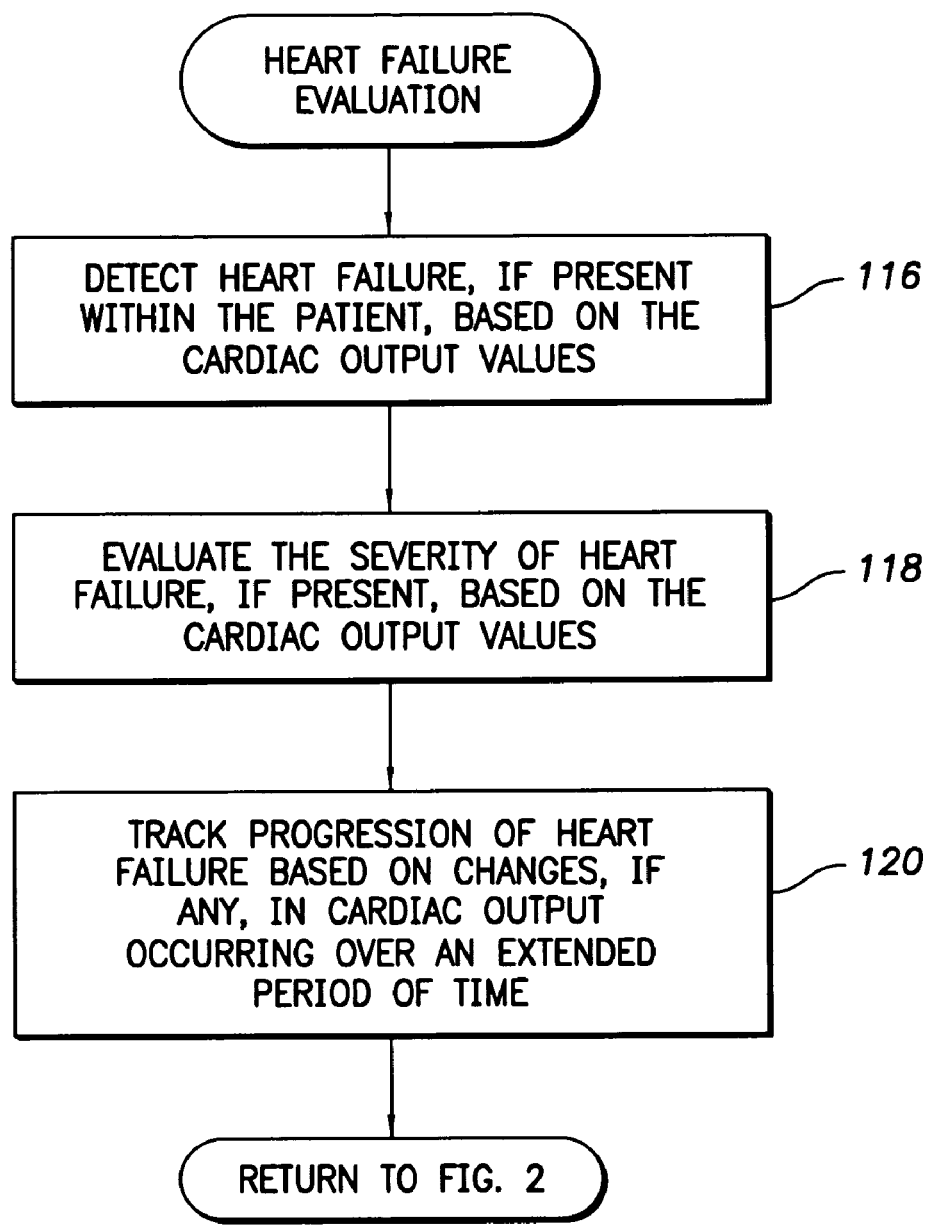
FIG. 4 is a flowchart providing an overview of a technique for evaluating heart failure based cardiac output for use with the method of FIG. 2.

FIG. 4 summarizes heart failure evaluation techniques that may be performed at step 110 of FIG. 2 based upon cardiac output values detected via thermal dilution. At step 116, heart failure, if present in the patient, is detected based on cardiac output. This may be performed by comparing the cardiac output against an initial predetermined threshold representative of the onset of heart failure. If cardiac output falls below the threshold, heart failure is presumed. If the pacer/ICD or external system is equipped to detect heart failure using alternative techniques such as EDP measurements, a final determination of whether the patient has heart failure may be made based on a combination of heart failure indices derived from various techniques. For example, a combined metric value can be generated based upon combinations of independently generated heart failure detection factors, with a final determination of whether heart failure has commenced based upon an analysis of that combined metric. See, for example, U.S. Pat. No. 6,645,153, to Kroll et al., entitled "System And Method For Evaluating Risk Of Mortality Due To Congestive Heart Failure Using Physiologic Sensors," which describes a technique for determining a CHF mortality risk metric based on a combination of estimated ventilatory response values and the slope of heart rate reserve as a function of predicted heart rates. See also: U.S. Pat. No. 6,438,408 to Mulligan et al., entitled "Implantable Medical Device for Monitoring Congestive Heart Failure."

Various alternative techniques for detecting heart failure are set forth in: U.S. patent application Ser. No. 11/014,276, of Min et al. entitled "System and Method for Predicting a Heart Condition Based on Impedance Values Using an Implantable Medical Device," filed Dec. 15, 2004, which is a continuation-in-part of U.S. patent application Ser. No. 10/810,437, of Bornzin et al., entitled "System and Method for Evaluating Heart Failure Based on Ventricular End-Diastolic Volume Using an Implantable Medical Device," filed Mar. 26, 2004 and U.S. patent application Ser. No. 10/346,809, of Min et al., entitled "System and Method for Monitoring Cardiac Function via Cardiac Sounds Using an Implantable Cardiac-Stimulation Device," filed Jan. 7, 2003.

At step, 118, the severity of heart failure is then evaluated based on cardiac output. Again, threshold values may be used, with different preprogrammed threshold values representative of different levels of the severity of heart failure, which potentially may be correlated with the aforementioned NYHA classifications. At step 120, the progression or regression of heart failure is tracked based on changes, if any, in cardiac output occurring over a period of time. In this regard, cardiac output values are stored following each thermal dilution analysis for comparison against subsequently derived values so as to permit detection of changes in the severity of heart failure over time. For example, cardiac output values may be calculated and stored on a periodic basis either once every week or daily, as clinically required, so that periodic changes can be detected. Insofar as progression tracking is concerned, the device need only compare the cardiac output values for the patient detected at various times and need not compare the values against any predetermined threshold values. In other words, insofar as progression or regression of heart failure is concerned, only changes in cardiac output are pertinent, the absolute magnitude of those values is not.

Figure 5:
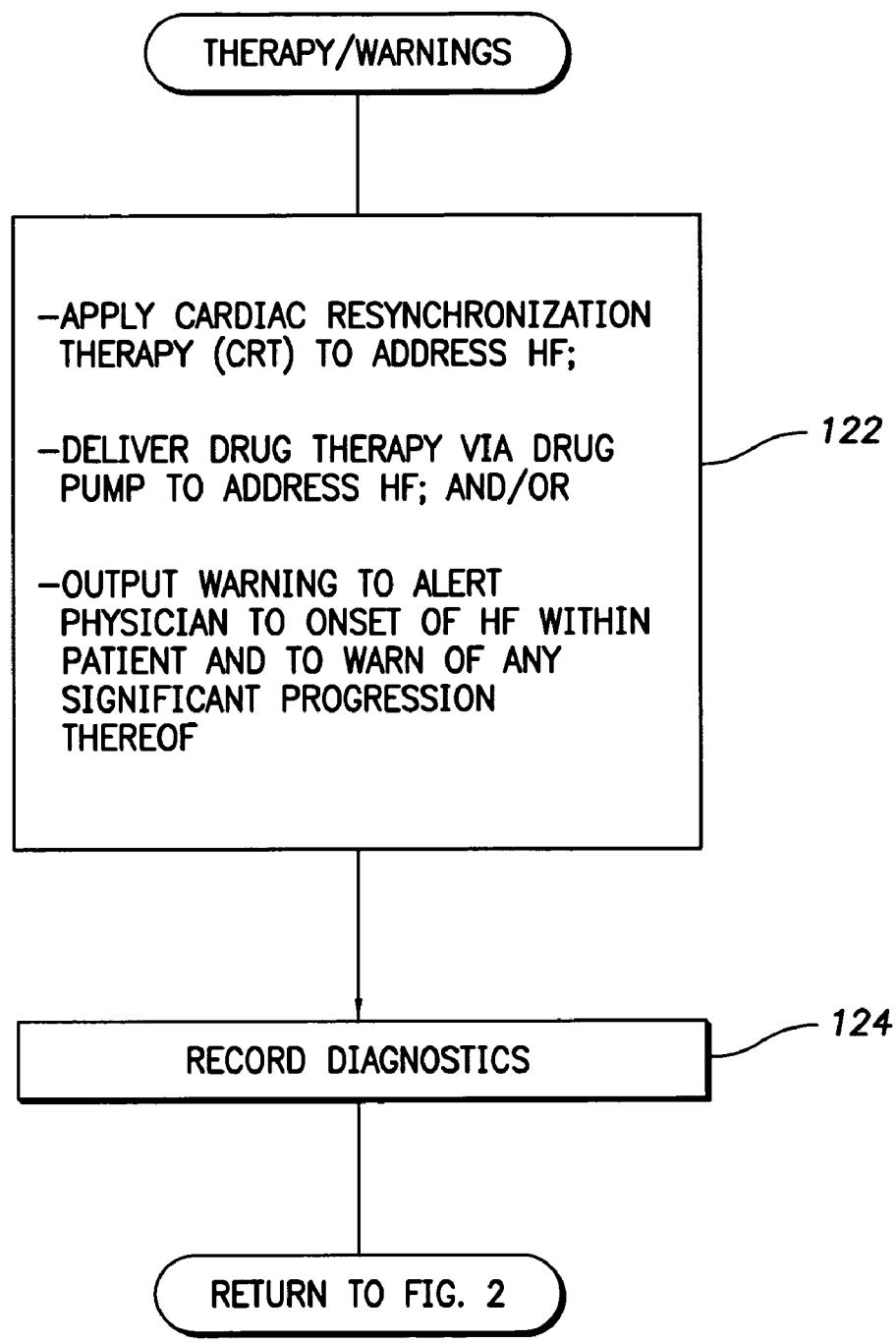
FIG. 5 is a flowchart providing an overview of therapy provided in response to the detection of heart failure for use with the method of FIG. 2.

Referring now to FIG. 5, therapy and warning signals, activated at step 112 of FIG. 2, will be summarized. At step 122, if the pacer/ICD is equipped to perform CRT, then CRT is activated/optimized to address heart failure. CRT and related therapies are discussed in the above-referenced patents to Mathis, et al., Kramer, et al., and Stahmann, et al. The degree of severity of heart failure may be used to control CRT pacing parameters such as the time delay between left and right ventricular pulses to, for example, so as to provide optimal rate for more severe heart failure. In addition, cardiac output may be used to optimize pacemaker atrioventricular (AV) delay.

Additionally, or alternatively, drug therapy specific to heart failure is delivered to the patient at step 122. Drug therapy may be delivered using an implanted drug pump, if so equipped. Exemplary heart failure medications include ACE inhibitors, diuretics, digitalis and compounds such as captopril, enalapril, lisinopril and quinapril. Depending upon the particular medication, alternative compounds may be required for use in connection with an implantable drug pump. Routine experimentation may be employed to identify medications for treatment of heart failure that are safe and effective for use in connection with an implantable drug pump. Dosages may be titrated based upon the severity of heart failure. Implantable drug pumps are discussed in U.S. Pat. No. 5,328,460 to Lord, et al., entitled "Implantable Medication Infusion Pump Including Self-Contained Acoustic Fault Detection Apparatus."

Therapy may also be controlled based on a combination of cardiac output and other heart failure measurements. For example, severely elevated pressures accompanied by substantially normal cardiac output might be treated by diuretics alone. However, if pressures are elevated and cardiac output is severely compromised, short term inotropic therapy may be performed in combination with diuretics to assure rapid clearance of excess fluid.

Warning signals generated at step 122 are displayed using the external system. For example, warning may be displayed to alert the person operating the external system as to the onset of heart failure in the patient or to warn of any significant progression in heart failure. At step 124, appropriate diagnostic information is stored within the memory of the implanted device and/or within memory of the external system. The external system may be directly networked with a centralized computing system for forwarding any warning signals or diagnostic data to the patient's personal physician. A system incorporating bedside monitoring units connected to a centralized external programmer system is described in U.S. Pat. No. 6,622,045 to Snell et al., "System and Method for Remote Programming of Implantable Cardiac Stimulation Devices."

Thus, FIGS. 2-5 describe cardiac output detection techniques and cardiac output-based heart failure detection and evaluation techniques that may be performed in accordance with the invention.

Figure 9:
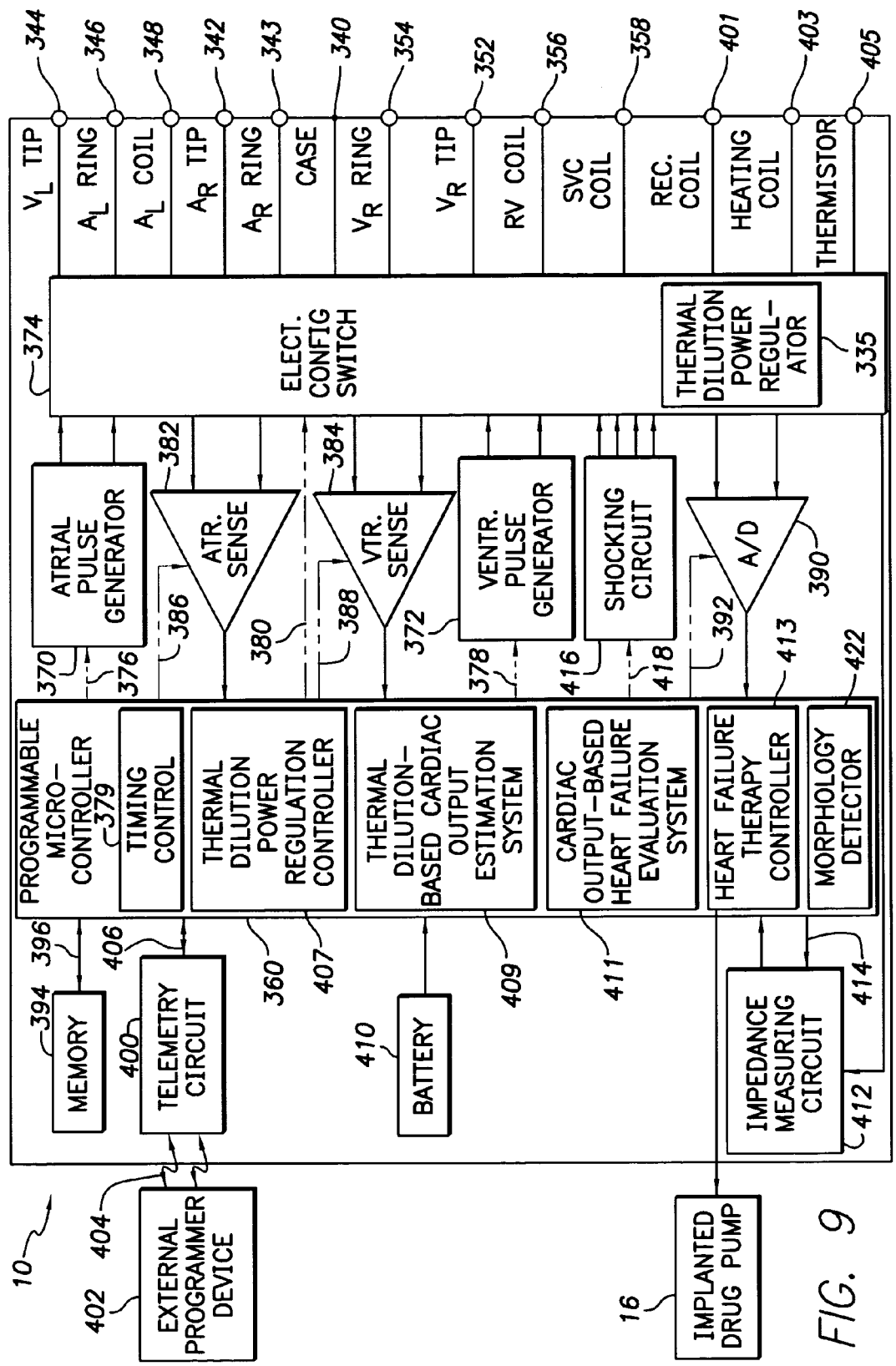
FIG. 9 is a functional block diagram of the pacer/ICD of FIG. 8, illustrating basic circuit elements that provide cardioversion, defibrillation and/or pacing stimulation in the heart and particularly illustrating components for detecting cardiac output and heart failure using the thermal dilution-based techniques of FIGS. 2-5.

A simplified block diagram of internal components of pacer/ICD 10 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned cardiac output detection and therapy.

Figure 6:
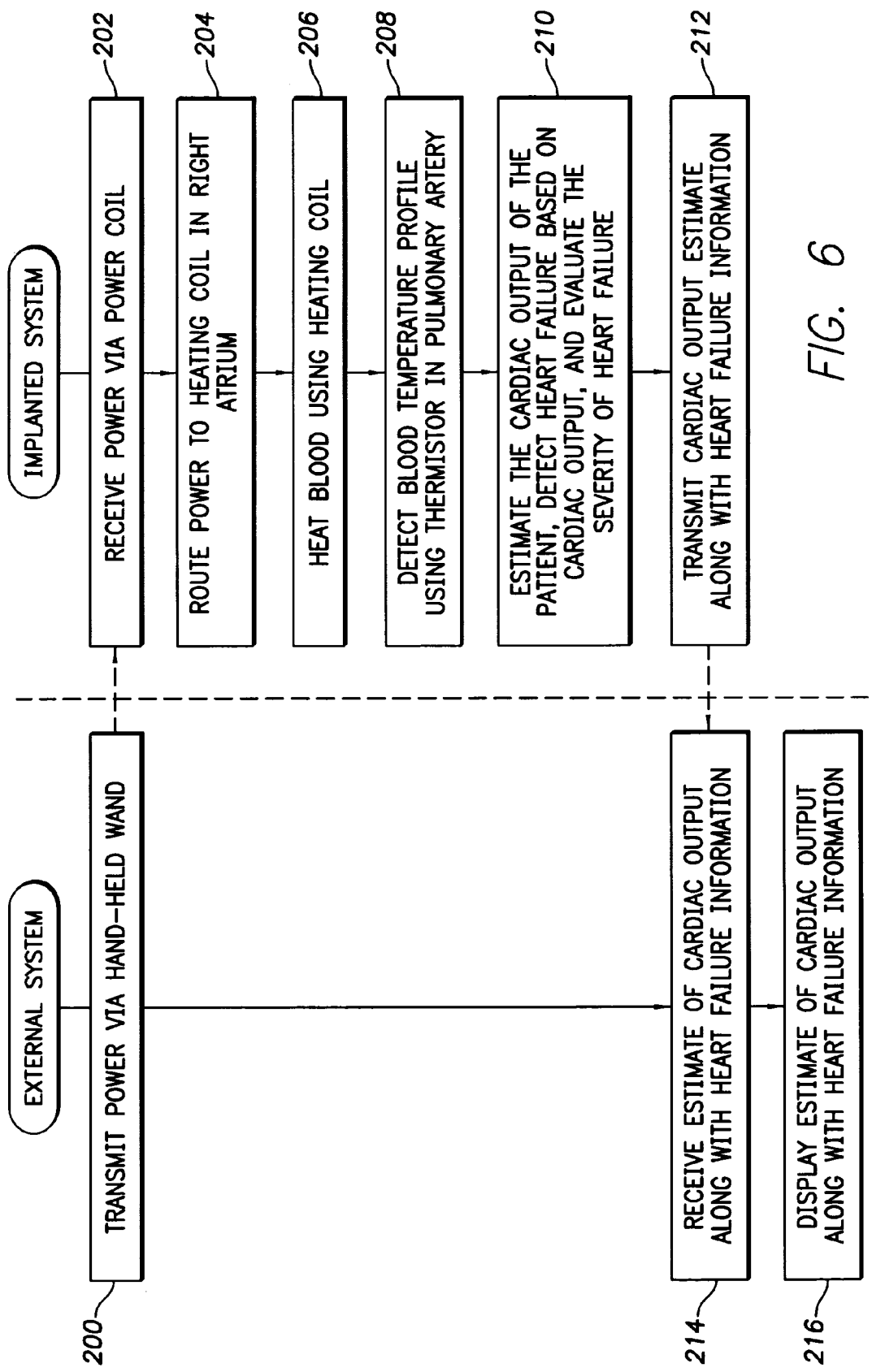
FIG. 6 is a flowchart illustrating steps of a first exemplary implementation of the general method of FIG. 2 wherein an external device calculates cardiac output based on thermal dilution information transmitted from the implanted device.

Referring first to FIG. 6, beginning at step 200, the external system transmits power via the hand-held wand, which is received, at step 202, by the subcutaneous power reception coil of the implanted system. At step 204, the power is routed to the heating coil implanted in the right atrium, which, at step 206, heats blood as it passes through the right atrium. At step 208, the implanted system detects the resulting thermal dilution blood temperature profile using the thermistor implanted in the pulmonary artery. At step 210, the implanted system estimates cardiac output, detects the onset of heart failure, and evaluates its severity, using techniques already described. At step 212, this information is transmitted via telemetry to the external system, which receives the data at step 214. At step 218, the estimated cardiac output is displayed along with information pertaining to the detection and evaluation of heart failure, if any, occurring with the patient. Although not shown in FIG. 6, the implanted system may also exploit the cardiac output estimate and heart failure evaluation to directly control therapy.

Figure 7:
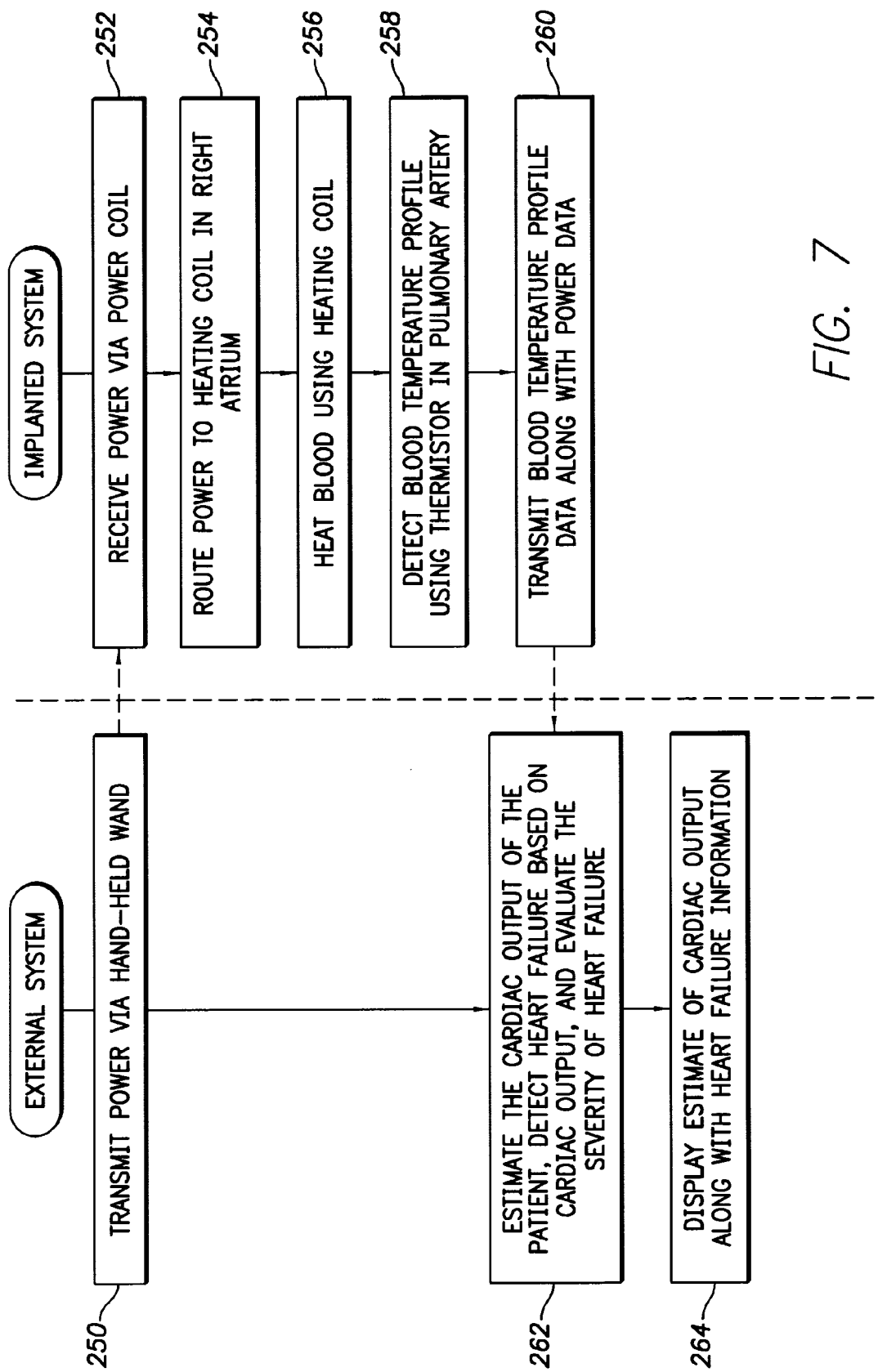
FIG. 7 is a flowchart illustrating steps of a second exemplary implementation of the general method of FIG. 2 wherein the implanted device itself calculates cardiac output based on thermal dilution.

Turning now to FIG. 7, at step 250, the external system likewise transmits power via the hand-held wand, which is received, at step 252, by the power reception coil of the implanted system. At step 254, the power is routed to the heating coil, which heats blood as it passes by, at step 256. At step 258, the implanted system detects the resulting thermal dilution blood temperature profile. At step 260, the temperature profile and the amount of power delivered to the heating coil are transmitted to the external system. At step 262, the external system then estimates cardiac output, detects the onset of heart failure, and evaluates its severity, using techniques already described. At step 264, the estimated cardiac output is displayed along with information pertaining to the detection and evaluation of heart failure, if any, occurring with the patient. Although not shown in FIG. 7, the external system may transmit its cardiac output estimate and its evaluation of heart failure back to the implanted system, which may then use that information to directly control therapy.

In the following section, an exemplary pacer/ICD will be described, which includes components for performing the above-described cardiac output estimation and heart failure evaluation techniques.

Exemplary Pacer/ICD for Use with Heating Coil

FIG. 8 provides a simplified block diagram of the pacer/ICD of FIG. 1, which is a dual-chamber stimulation device capable of treating both fast and slow arrhythmias with stimulation therapy, including cardioversion, defibrillation, and pacing stimulation, as well as capable of estimating cardiac output via thermal dilution and detecting heart failure, evaluating its severity, tracking the progression thereof, and controlling the delivery of therapy and warnings in response thereto. To provide atrial chamber pacing stimulation and sensing, pacer/ICD 10 is shown in electrical communication with a heart 312 by way of a left atrial lead 320 having an atrial tip electrode 322 and an atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 324 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328. With this configuration, biventricular pacing can be performed. Although only three leads are shown in FIG. 8, it should also be understood that additional stimulation leads (with one or more pacing, sensing and/or shocking electrodes) may be used in order to efficiently and effectively provide pacing stimulation to the left side of the heart or atrial cardioversion and/or defibrillation.

In addition to the electrode components already described, the CS lead 324 also includes heating coil 22 for heating blood in the RA based on power delivered by the subcutaneous receive coil 18. The receive coil is, in this implementation, coupled directly to the pacer/ICD. The pacer/ICD includes internal components for regulating power received via the subcutaneous coil. The regulated power is then routed along the CS lead to the heating coil for heating blood in the RA. In alternative implementations, the heating coil may be mounted to one of the other leads, i.e. leads 320 or 330. In still other implementations, a separate lead is provided for the heating coil.

Right ventricular lead 330 additionally includes a pulmonary artery portion 331, which includes thermistor 12. Pulmonary artery portion 331 is sized, shaped and configured to position the thermistor in the pulmonary artery as shown. A balloon may be used to float the thermistor into place, which is then deflated to allow unimpeded blood flow, in accordance with otherwise conventional techniques. Signals representative of temperature detected by the thermistor are routed back along pulmonary artery portion 331 to the main portion of lead 330 then on to the pacer/ICD for processing.

A simplified block diagram of internal components of pacer/ICD 10 is shown in FIG. 9. While a particular pacer/ICD is shown, this is for illustration purposes only, and one of skill in the art could readily duplicate, eliminate or disable the appropriate circuitry in any desired combination to provide a device-capable of treating the appropriate chamber(s) with cardioversion, defibrillation and pacing stimulation as well as providing for the aforementioned apnea detection and therapy.

The housing 340 for pacer/ICD 10, shown schematically in FIG. 9, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, 344, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes at least a left ventricular tip terminal ($V_L$ TIP) 344, a left atrial ring terminal ($A_L$ RING) 346, and a left atrial shocking terminal ($A_L$ COIL) 348, which are adapted for connection to the left ventricular ring electrode 326, the left atrial tip electrode 327, and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($R_V$ COIL) 356, and an SVC shocking terminal (SVC COIL) 358, which are adapted for connection to the right ventricular tip electrode 332, right ventricular ring electrode 334, the RV coil electrode 336, and the SVC coil electrode 338, respectively.

Additionally, terminals are shown for receiving power from the subcutaneous receive coil (terminal 401), forwarding regulated power to the heating coil (terminal 403) and for receiving signals from the thermistor (terminal 405).

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 9, an atrial pulse generator 370 and a ventricular/impedance pulse generator 372 generate pacing stimulation pulses for delivery by the right atrial lead 320, the right ventricular lead 330, and/or the coronary sinus lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

Switch 334 also includes a power regulator 335 for regulating power received from the subcutaneous coil for routing to the heating coil, under the control of the microcontroller.

Atrial sensing circuits 382 and ventricular sensing circuits 384 may also be selectively coupled to the right atrial lead 320, coronary sinus lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, pacer/ICD 10 utilizes the atrial and ventricular sensing circuits, 382 and 384, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the right atrial lead 320, the coronary sinus lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

In addition, the stimulation device may be configured to perform Automatic Mode Switching (AMS) wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a nontracking mode precluding its triggering ventricular outputs in response to sensed atrial events. Numerous other device modes of operation are possible, each represented by standard abbreviations of this type.

Advantageously, the operating parameters of the implantable pacer/ICD 10 may be non-invasively programmed into the memory 394 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 394) to be sent to the external device 402 through an established communication link 404. Pacer/ICD 10 further includes an accelerometer or other physiologic sensor 408, commonly referred to as a "rate-responsive" sensor because it is typically used to adjust pacing stimulation rate according to the exercise state of the patient. However, the physiological sensor 408 may further be used to detect changes in cardiac output, changes in the physiological condition of the heart, or diurnal changes in activity (e.g., detecting sleep and wake states) and to detect arousal from sleep. Accordingly, the microcontroller 360 responds by adjusting the various pacing parameters (such as rate, AV Delay, V-V Delay, etc.) at which the atrial and ventricular pulse generators, 370 and 372, generate stimulation pulses. While shown as being included within pacer/ICD 10, it is to be understood that the physiologic sensor 408 may also be external to pacer/ICD 10, yet still be implanted within or carried by the patient. A common type of rate responsive sensor is an activity sensor incorporating an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient an, in particular, is capable of detecting arousal from sleep or other movement.

The pacer/ICD additionally includes a battery 410, which provides operating power to all of the circuits shown in FIG. 9. The battery 410 may vary depending on the capabilities of pacer/ICD 10. If the system only provides low voltage therapy, a lithium iodine or lithium copper fluoride cell may be utilized. For pacer/ICD 10, which employs shocking therapy, the battery 410 must be capable of operating at low current drains for long periods, and then be capable of providing high-current pulses (for capacitor charging) when the patient requires a shock pulse. The battery 410 must also have a predictable discharge characteristic so that elective replacement time can be detected. Accordingly, pacer/ICD 10 is preferably capable of high voltage therapy and appropriate batteries.

As further shown in FIG. 9, pacer/ICD 10 is shown as having an impedance measuring circuit 412 which is enabled by the microcontroller 360 via a control signal 414. Herein, impedance is primarily detected for use in evaluating respiration. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

Microcontroller 360 also includes various components directed to (1) controlling the regulation of power delivered to the heating coil; (2) estimating cardiac output based on the temperature signals received from the thermistor; and (3) detecting, evaluating and treating of heart failure based on the cardiac output estimation. More specifically, a power regulation controller 407 operates to control power regulator circuit 335 to regulate power received from subcutaneous coil 18 (FIGS. 1 and 8) for delivery to the heating coil 22 (also FIGS. 1 and 8). As noted, power delivered to the heating coil is regulated so as to prevent power spikes that might damage tissue or blood. The power regulator controller also records the amount of power delivered to the heating coil for use as the Power$_{in}$ value in the estimation of cardiac output (FIG. 3). Power may also be regulated so that the power delivered to the heating coil is substantially uncorrelated with respiration, as already explained. If any additional, i.e. "left over", power is available, it may potentially be used to partially recharge battery 410 or reform capacitors of shocking circuit 416. See, for example, U.S. Pat. No. 6,505,077, to Kast et al., entitled "Implantable Medical Device with External Recharging Coil Electrical Connection" and U.S. Pat. No. 5,733,313 to Barreras, Sr. et al., entitled "RF Coupled, Implantable Medical Device with Rechargeable Back-Up Power Source."

A thermal dilution-based cardiac output estimation system 409 estimates cardiac output based on the Power$_{in}$ value in combination with thermal dilution profile data received from thermistor 12 (FIGS. 1 and 8) via terminal 405 using the techniques of FIG. 3. Alternatively, the Power$_{in}$ value and the thermal dilution profile data may be transmitted via telemetry circuit 400 to the external system for processing therein. If so, then a thermal dilution-based cardiac output estimation system need not be provided in the pacer/ICD. A cardiac output-based heart failure evaluation system 411 evaluates heart failure, if any, within the patient based on cardiac output using techniques described above in connection with FIG. 4. Alternatively, this evaluation may be performed by the external system and, if so, then a cardiac output-based heart failure evaluation system need no be provided in the pacer/ICD.

The microcontroller also includes a heart failure therapy controller 413, which controls the delivery of therapy in response to heart failure using techniques summarized in FIG. 5. This includes controlling a drug pump, if so equipped, to deliver any appraise medications. Note that if the pacer/ICD does not include internal components for detecting heart failure, then the heart failure therapy controller operates based on any heart failure data received from the external system via telemetry circuit 400.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller. Collectively, the subcutaneous power reception coil, the power regulation controller and the power regulator comprise an implantable power reception system. The heating coil, thermistor, and thermal dilution-based cardiac output estimation system comprise an implantable cardiac output detection system.

Exemplary External Electromagnetic Induction Power Delivery System

Figure 10:
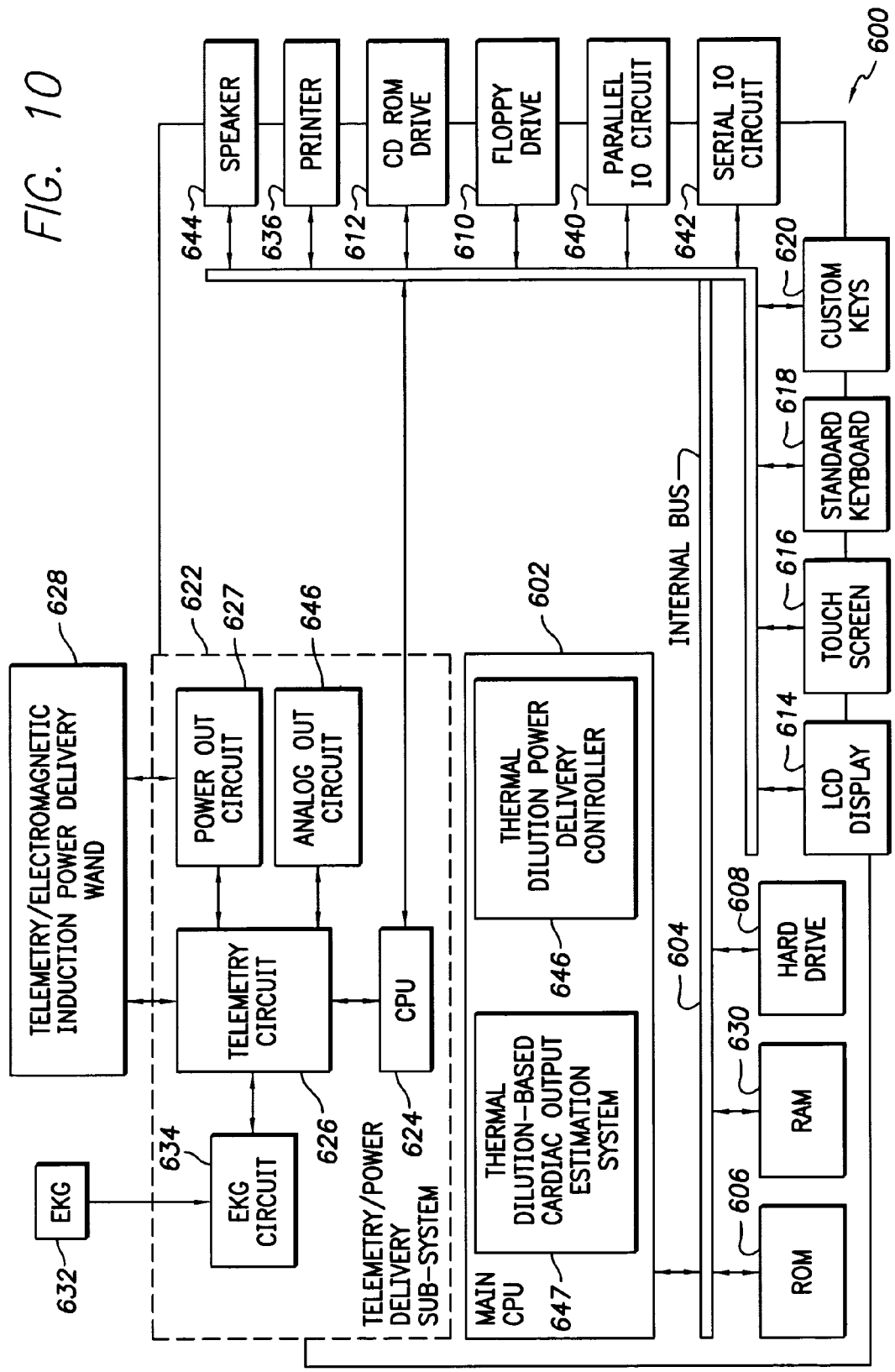
FIG. 10 is a functional block diagram of an external programmer/bedside monitoring device for delivering power to the implanted system of FIGS. 8-9 and for calculating and/or displaying cardiac output values calculated using the techniques of FIGS. 2-5.

FIG. 10 illustrates pertinent components of an external programmer for use in programming an implantable system such as a pacemaker or ICD and for delivering power to the implanted system via electromagnetic induction for thermal dilution analysis. The programmer permits a physician or other user to program the operation of the implanted device and to retrieve and display information received from the implanted device such as IEGM data and device diagnostic data. Additionally, the external programmer receives and displays EKG data from separate external EKG leads that may be attached to the patient. Depending upon the specific programming of the external programmer, programmer 600 may also be capable of processing and analyzing data received from the implanted device and from the EKG leads to, for example, render preliminary diagnosis as to medical conditions of the patient or to the operations of the implanted device. As noted, the programmer is also configured to provide power to the implantable system for use in thermal dilution analysis of the cardiac output of a patient.

Now, considering the components of programmer 600, operations of the programmer are controlled by a CPU 602, which may be a generally programmable microprocessor or microcontroller or may be a dedicated processing device such as an application specific integrated circuit (ASIC) or the like. Software instructions to be performed by the CPU are accessed via an internal bus 604 from a read only memory (ROM) 606 and random access memory 630. Additional software may be accessed from a hard drive 608, floppy drive 610, and CD ROM drive 612, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 614 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 616 overlaid on the LCD display or through a standard keyboard 618 supplemented by additional custom keys 620, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various devices are programmed. Typically, the physician initially controls the programmer 600 to retrieve data stored within any implanted devices and to also retrieve EKG data from EKG leads, if any, coupled to the patient. To this end, CPU 602 transmits appropriate signals to a telemetry subsystem 622, which provides components for directly interfacing with the implanted devices, and the EKG leads. Telemetry subsystem 622 includes its own separate CPU 624 for coordinating the operations of the telemetry subsystem. Main CPU 602 of programmer communicates with telemetry subsystem CPU 624 via internal bus 604. Telemetry subsystem additionally includes a telemetry circuit 626 connected to telemetry/power wand 628, which, in turn, receives and transmits signals electromagnetically from a telemetry unit of the implanted device. The telemetry/power wand is placed over the chest of the patient near the implanted device to permit reliable transmission of data between the telemetry wand and the implanted device.

The telemetry/power wand also delivers power to the receive coil of the implantable system for thermal dilution analysis of cardiac output. To this end, the programmer also includes a power out circuit 627, which controls delivery of power to the wand. Alternatively, separate wands may be provided for telemetry and for power delivery.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the implanted devices is stored by external programmer 600 either within a random access memory (RAM) 630, hard drive 608 or within a floppy diskette placed within floppy drive 610. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 600, the implanted devices may be further controlled to transmit additional data in real time as it is detected by the implanted devices, such as additional IEGM data lead impedance data, and the like. Additionally, or in the alternative, telemetry subsystem 622 receives EKG signals from EKG leads 632 via an EKG processing circuit 634. As with data retrieved from the implanted device itself, signals received from the EKG leads are stored within one or more of the storage devices of the external programmer. Typically, EKG leads output analog electrical signals representative of the EKG. Accordingly, EKG circuit 634 includes analog to digital conversion circuitry for converting the signals to digital data appropriate for further processing within programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from the external EKG leads. Data retrieved from the implanted devices includes parameters representative of the current programming state of the implanted devices. Under the control of the physician, the external programmer displays the current programming parameters and permits the physician to reprogram the parameters. To this end, the physician enters appropriate commands via any of the aforementioned input devices and, under control of CPU 602, the programming commands are converted to specific programming parameters for transmission to the implanted devices via telemetry wand 628 to thereby reprogram the implanted devices. Prior to reprogramming specific parameters, the physician may control the external programmer to display any or all of the data retrieved from the implanted devices or from the EKG leads, including displays of ECGs, IEGMs, and statistical patient information. Any or all of the information displayed by programmer may also be printed using a printer 636.

Programmer 600 also includes a modem 638 to permit direct transmission of data to other programmers via the public switched telephone network (PSTN) or other interconnection line, such as a T1 line or fiber optic cable. Depending upon the implementation, the modem may be connected directly to internal bus 604 may be connected to the internal bus via either a parallel port 640 or a serial port 642. Other peripheral devices may be connected to the external programmer via parallel port 640 or a serial port 642 as well. Although one of each is shown, a plurality of input output (IO) ports might be provided. A speaker 644 is included for providing audible tones to the user, such as a warning beep in the event improper input is provided by the physician. Telemetry subsystem 622 additionally includes an analog output circuit 646 for controlling the transmission of analog output signals, such as IEGM signals output to an EKG machine or chart recorder.

For the purposes of thermal dilution analysis, the main CPU includes a thermal dilution-based power delivery controller 646, which controls the delivery of power via power out circuit 627 to wand 628. If the implanted device is not equipped to estimate cardiac output based on thermal dilution data, then the device transmits the data to the external programmed, which received the data via wand 628. The programmed then uses a thermal dilution-based cardiac output estimation system 647 to estimate cardiac output based on the data, using the techniques of FIG. 3. Data pertaining to cardiac output is displayed via LCD display 614 for review by the physician. Other components of the main CPU may additionally exploit the estimate of cardiac output to detect heart failure, evaluate its severity and track its progression, using the techniques of FIG. 4. Data pertaining to heart failure is also displayed via the LCD display for review by the physician. The physician may then reprogram any parameters of the implanted device to address the heart failure.

Thus, with the programmer configured as shown, a physician or other user operating the external programmer is capable of retrieving, processing and displaying a wide range of information received from the implanted devices and to reprogram the implanted devices if needed. The descriptions provided herein with respect to FIG. 10 are intended merely to provide an overview of the operation of programmer and are not intended to describe in detail every feature of the hardware and software of the device and is not intended to provide an exhaustive list of the functions performed by the device.

Note that, for the purposes of power delivery for thermal dilution analysis, a full device programmer need not be used. Rather it is sufficient to provide an external device capable of delivering power via electromagnetic induction to an implanted power receive coil. A full function programmer has been described herein for the sake of completeness. Note a device may be implemented that does not require that power be delivered by electromagnetic induction to an implanted power receiver coil. In this case only an internal battery is used as power source. With such a system, it is possible to perform a limited number of estimates of cardiac output using only an internal battery power source. In yet another alternative embodiment, electromagnetic induction may be used to charge the battery and thus enabling cardiac outputs with power from a rechargeable internal battery. A large number of cardiac outputs are possible over the lifetime of a rechargeable system.

What have been described thus far are various systems and methods for evaluating cardiac output via thermal dilution analysis wherein power is delivered to the implantable system from an external source via electromagnetic induction. In the following, alternative systems and methods for evaluating cardiac output via thermal dilution analysis will be described wherein power is delivered from the external source via ultrasound. As some of the features of the ultrasound-based techniques are similar to those of the electromagnetic induction-based techniques already described, these features will not be re-described in detail rather only pertinent difference will be described in detail.

Overview of Implantable System Employing Ultrasound

Figure 11:
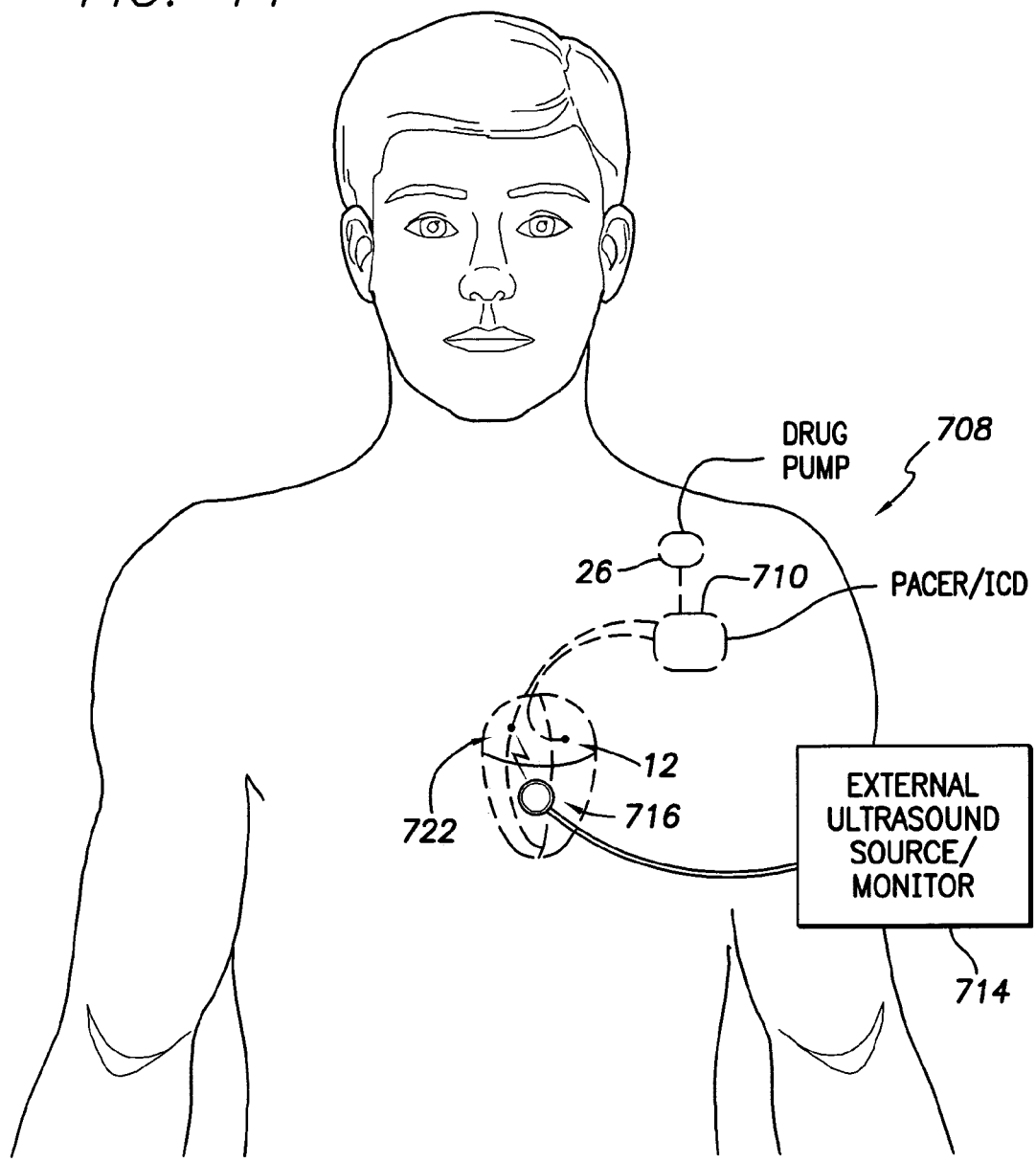
FIG. 11 illustrates pertinent components of a second embodiment of an implantable medical system having a pacemaker or ICD capable of detecting and evaluating heart failure based on thermal dilution cardiac output measurements using power provided from an external source using ultrasound.

FIG. 11 illustrates an implantable medical system 708 capable of estimating cardiac output via thermal dilution techniques using power delivered via ultrasound from an external source. In the preferred implementation, the system is further capable of detecting heart failure based on changes in cardiac output, evaluating its severity, tracking its progression and delivering appropriate therapy. Implantable medical system 708 includes a pacer/ICD 710 or other cardiac stimulation device that incorporates internal components (shown individually in FIG. 16) for estimating cardiac output based on a thermal dilution blood temperature profile received from a temperature sensor 12 implanted in the pulmonary artery, which may be the same as the sensor of FIG. 1. Briefly, power for performing thermal dilution analysis is provided by an ultrasound-based external power source/monitor 714. Power (initially derived from an AC wall socket) is routed to an ultrasound power delivery wand 716, which is held near the chest of the patient. Hand-held wand 716 generates a beam of ultrasound that irradiates an ultrasound-responsive heating element 722 positioned within the right atrium, which, in turn, generates heat in response to ultrasound. The heating element may be formed, for example, of an acoustic absorber material such as polyurethane RP-6401. Optionally, an ultrasound transducer 723 producing an electrical signal which varies predictably with incident ultrasound power may be part of the heating element. With a measurement of available ultrasound power, and with knowledge of the absorption coefficient of the heating element, the heat power introduced into the right atrium may be accurately known. In any case, the heating element heats up in response to the beam of ultrasound, thus also heating a portion of blood passing through the right atrium. The heated blood is pumped from the right atrium into the right ventricle then pumped through the pulmonary artery past thermistor 12, which senses a resulting thermal dilution temperature profile. The shape and amplitude of the temperature profile provides an indication of cardiac output. Signals representative of the thermal dilution profile are routed from the thermistor to pacer/ICD 710, which estimates cardiac output based upon the thermal dilution profile or forwards the thermal dilution profile data to external power source/monitor 714 for estimation of cardiac output therein. Exemplary techniques for estimating cardiac output based upon a thermal dilution temperature profile were described above, particularly with reference to FIG. 3.

Figure 15:
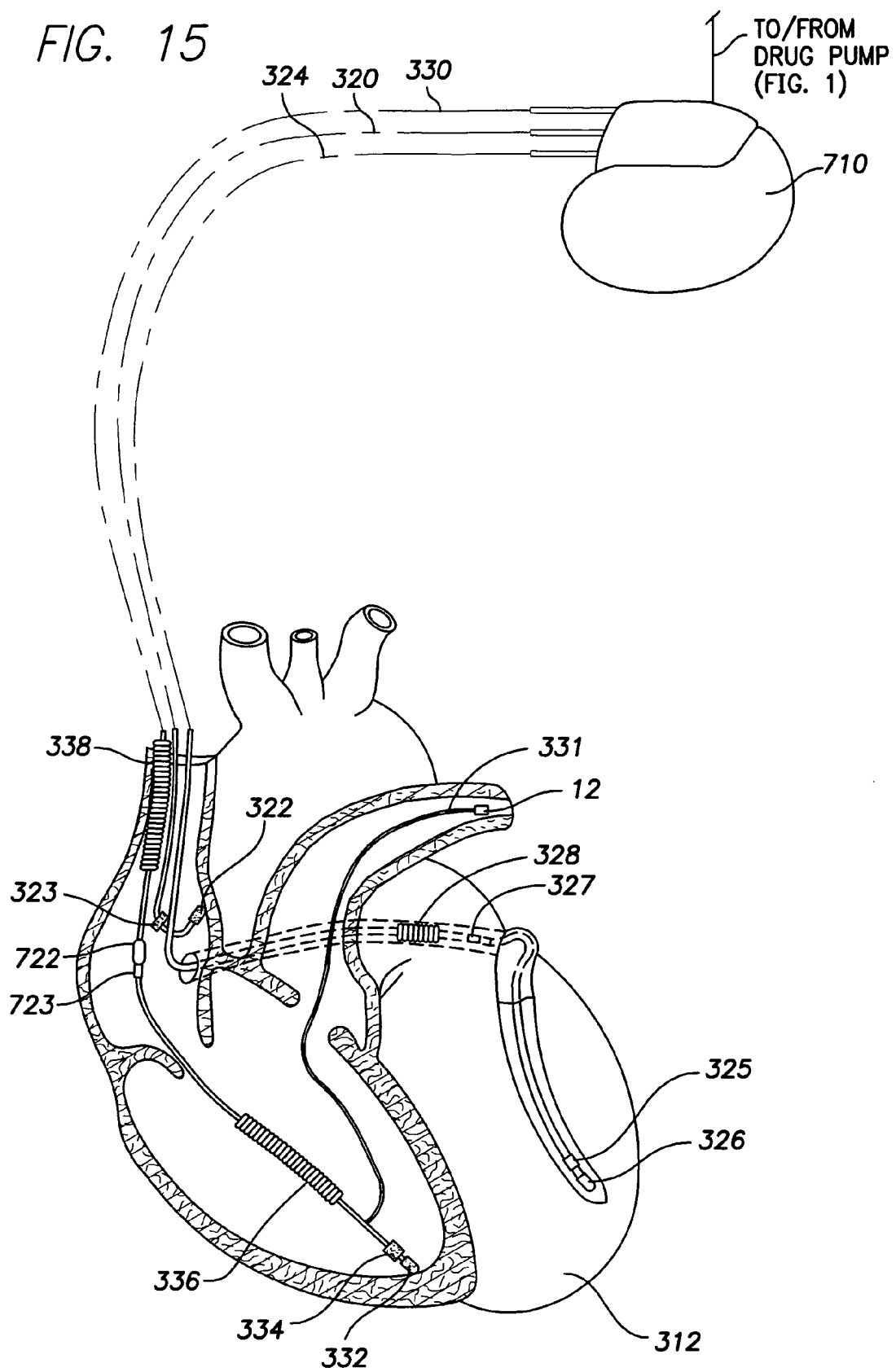
FIG. 15 is a simplified, partly cutaway view, illustrating the pacer/ICD of FIG. 11 along with at full set of leads implanted into the heart of the patient and also illustrating an ultrasound-responsive heating element in the RA and a thermistor in the pulmonary artery.

Thus, power provided by the external power source via ultrasound is used to heat blood for the purposes of the thermal dilution analysis of cardiac output so that the power resources of the pacer/ICD itself may be conserved for other uses, such as delivering pacing therapy or cardioversion shocks to the patient via the leads implanted in the heart. Only a pair of exemplary leads is shown within FIG. 11; a full set of leads and electrodes is illustrated in FIG. 15. As already been explained, once the cardiac output of the patient has been estimated via thermal dilution analysis, the resulting cardiac output values are then used to detect and evaluate heart failure, if any, within the patient so that appropriate warning signals may be generated and/or appropriate therapy may be automatically initiated. As with the embodiment of FIG. 1, the implantable system of FIG. 11 may be equipped with a drug pump 26 capable of the delivering drug therapy in an attempt to address heart failure. Additionally, as explained, the pacer/ICD is capable of performing a wide variety of otherwise conventional pacing and/or defibrillation functions, such as delivering pacing is response to an arrhythmia or generating and delivering defibrillation shocks in response to fibrillation.

Hence, FIG. 11 provides an overview of an implantable system capable of estimating cardiac output via thermal dilution analysis based upon power received via ultrasound from an external source and further capable of detecting and evaluating heart failure and delivering appropriate warnings and therapy. Embodiments may be implemented that do not necessarily perform all of these functions or which do need include all the components shown in FIG. 11. In many cases, for example, no drug pump is implanted. No attempt is made herein to describe all possible combinations of components that may be provided in accordance with the general principles of the invention. As with FIG. 1, implanted components of FIG. 11 are shown in phantom lines so as to be clearly distinguished from the external components of the system. The particular shape, size and location of the implanted components are merely illustrative and may not necessarily correspond to actual implant locations.

Thermal Dilution Analysis Using Ultrasound

Figure 12:
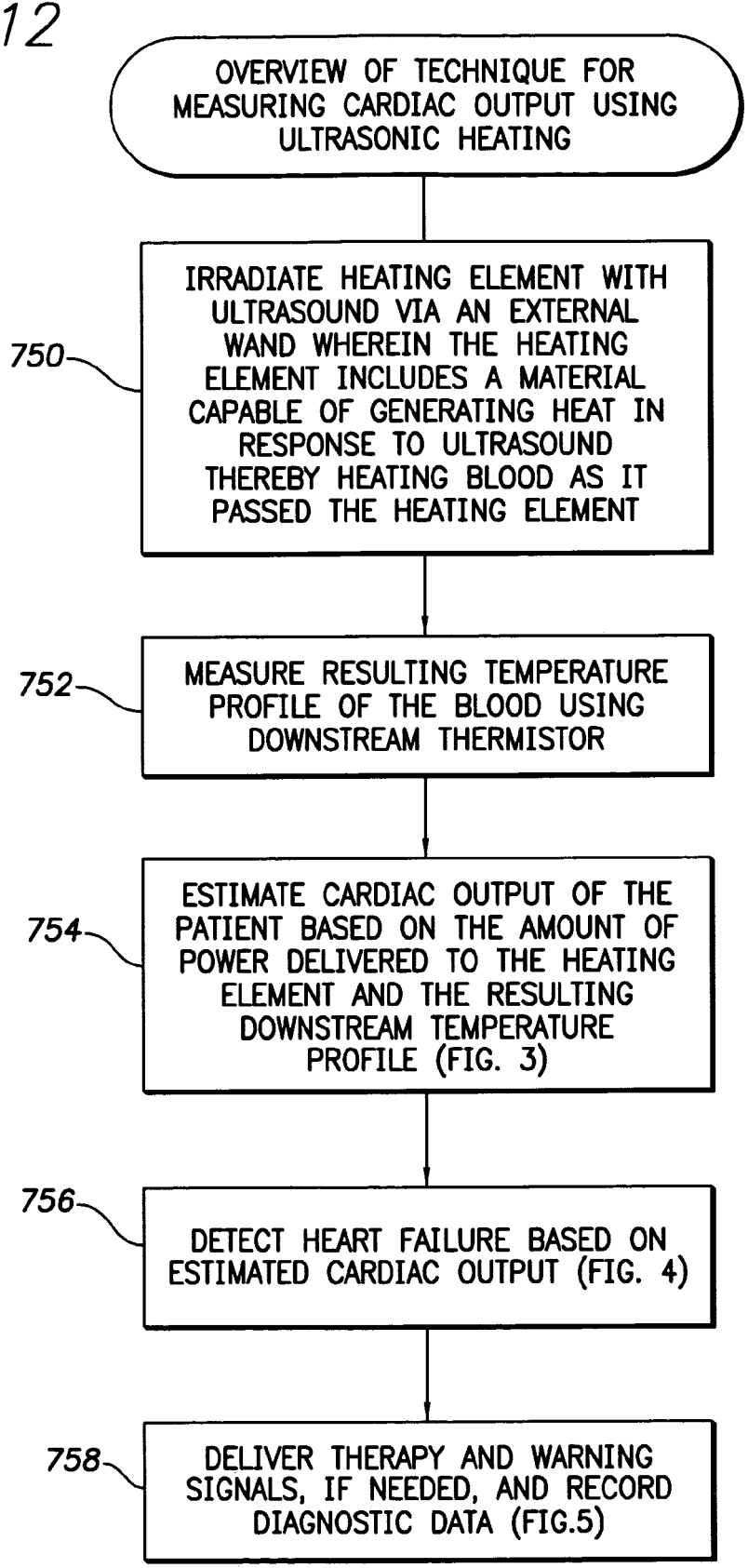
FIG. 12 is a flowchart providing an overview of a method for detecting cardiac output via thermal dilution for use by the system of FIG.

FIG. 12 summarizes the detection of cardiac output and heart failure using ultrasound-based thermal dilution analysis, which may be performed by the system of FIG. 11. Beginning at step 750, the ultrasound-responsive heating element of the implantable system is irradiated by ultrasound generated from the wand of the external power source. As noted, the ultrasound-responsive heating element is a device capable of generating heat in response to ultrasound. In one example, the heating element is formed of an acoustic absorber material that increases in temperature in response to ultrasound, such as polyurethane RP-6401. In another example, a special polyurethane rubber provided by Applied Polymer Technology Ltd. of Gloucestershire, England may be employed. For a discussion of uses of this material within applications external to the body, see: Bell, "From Securing Stealth to Ensuring Health: Making Ultrasound Treatment Ultra-Safe," Ingenia, Issue 19, May/June 2004, pages 25-29. See, also, materials provided by Precision Acoustics Ltd. of Dorchester, England. In general, any of a variety of materials employed in stealth technology for use with submarines may potentially be employed since such materials are typically highly effective as acoustic absorbers at ultrasound frequencies. Various types of acoustic absorption polymers are discussed in U.S. Patent Application: 2003/0087802 of Urry, entitled "Acoustic-Absorption Polymers and Their Methods of Use." Note also that heating element may be a composite formed of two or more materials that, in combination, generate heat in response to ultrasound. In any case, routine experimentation is performed to identify suitable acoustic absorber materials that are biocompatible for implant within the heart. For any acoustic absorber material that is not biocompatible, it may nevertheless be feasible to seal the material within an enclosure that is biocompatible.

Optionally, a transducer 723 which produces an electrical signal which varies predictably with ultrasound power may be part of the heating element. For example cylindrical piezoelectric transducers such as are known in the art may be employed. See, for example, "Integrated Catheter for 3-D Intracardiac Echocardiography and Ultrasound Ablation" by Kenneth L. Gentry and Stephen W. Smith in IEEE Transactions on Ultrasonics, Ferroelectrics, and Frequency Control, vol. 51, no. 7, July 2004 799.

Alternatively, the heating element may incorporate pyroelectric materials that generate electricity in response to ultrasound, with the electricity then used to heat a component of the heating element, such as a simple heating coil, which in turn heats the blood. This embodiment has the additional benefit that an electrical signal is generated which is directly related to the heat power in the heating element. This signal may be measured and through this measurement, the delivered heat power may be known. When using devices that generate electricity in response ultrasound, care should be taken to ensure that any electrical signals generated within the heating element do not adversely affect myocardial tissue or interfere with the otherwise routine detection of electrical cardiac signals by sensing electrodes within the heart. To this end, the electrical components of the heating element should be electrically insulated. A heating element that directly converts ultrasound to heat (such as the aforementioned polymers) is generally preferred since these issues are avoided. As can be appreciated, a variety of devices or techniques may potentially be employed to convert ultrasound to heat. Routine experimentation may be performed to identify optimal shapes, sizes and orientations of heating elements for use in the right atrium, which maximize the amount of heat generated for heating blood while minimizing interruption with blood flow.

As noted above, blood is preferably heated by about 4-5 C to allow for reliable detection of cardiac output using thermal dilution techniques. Accordingly, about 10 watts of heating is preferably provided by the heating element. The amount of power generated by the power delivery wand (in the form of ultrasound energy) is thereby selected so as to achieve at least 10 W of heating by the heating element. This depends, of course, on the size, shape, location and orientation of the heating element, as well as the efficiency by which the heating element converts ultrasound energy and heat. Routine experimentation may be performed to determine the amount of power to be generated by the ultrasound power delivery wand based upon the particular heating element to be used and its location and orientation within the right atrium. Insofar as polyurethane RP-6401 is concerned, it absorbs 100 dB/cm in response to ultrasound at a frequency of 5 MHz. For a heating element formed of RP-6401 that presents a surface perpendicular to the ultrasound beam with a cross-section of about 1 $cm^2$, the ultrasound beam should provide at least 10 W/$cm^2$ of power. (Currently, the maximum power intensity allowed during diagnostic ultrasound by the U.S. Food and Drug Administration is 720 mW/$cm^2$. Accordingly, a variance may be required for use with the invention.) The polyurethane material provided by Applied Polymer Technology Ltd., discussed above, is said to absorb more than 80% of ultrasonic power within 1 mm of the front surface its absorber, thus corresponding to 140 dB/cm absorption at ultrasonic frequencies. Hence, with a heating element formed using that material, a less intense ultrasound been may instead be employed while still achieving the requisite amount of heating.

As explained above, internal body temperature can vary by about 0.1 C, primarily because of respiration. Accordingly, it is preferred that the power delivered to the heating element via ultrasound be delivered in a manner that is uncorrelated with respiration so that respiratory influences can be cancelled out, using one of the techniques discussed above. Patient respiration may also be tracked, using otherwise conventional techniques, to aid in ensuring that the power delivered to the element is uncorrelated with respiration.

At step 752, the thermistor implanted within the pulmonary artery measures the resulting temperature profile of the blood. Suitable thermistors are discussed above. At step 754, cardiac output is estimated based on the power delivered via ultrasound to the heating element in combination with the resulting downstream temperature profile measured by the thermistor. The technique for estimating cardiac output described above with reference to FIG. 3 may be used. Otherwise conventional signal processing techniques may be exploited to maintain a suitable signal to noise ratio within the temperature profile so as to allow the amount of energy needed during the heating process to be minimized while still allowing cardiac output to be reliably estimated. At step 756, heart failure, if occurring within the patient, is then detected and its progression tracked based on the estimated cardiac output using, for example, the technique described above in connection with FIG. 4. The detection of heart failure based on cardiac output may be supplemented by other heart failure detection techniques, such as those based on EDP. Steps 754 and 756 are performed, depending upon the particular implementation, by (1) the implanted system based on data it receives from the thermistor; (2) the external system based on data transmitted from the implanted system; or (3) both. An exemplary technique wherein the implanted device estimates cardiac output and detects heart failure and then transmits that information to the external system is summarized below with reference to FIG. 13. An exemplary technique wherein the external system estimates cardiac output and detects heart failure based on thermal dilution profile data transmitted from the implanted system is summarized below with reference to FIG. 14. Internal components of exemplary implantable systems and external systems are described below with reference to FIGS. 15-17. At step 758, therapy, if needed, is delivered to the patient and appropriate warning signals are generated and diagnostic data is recorded. Therapy, warning signals and storage of diagnostic data was described with reference to FIG. 5.

Figure 13:
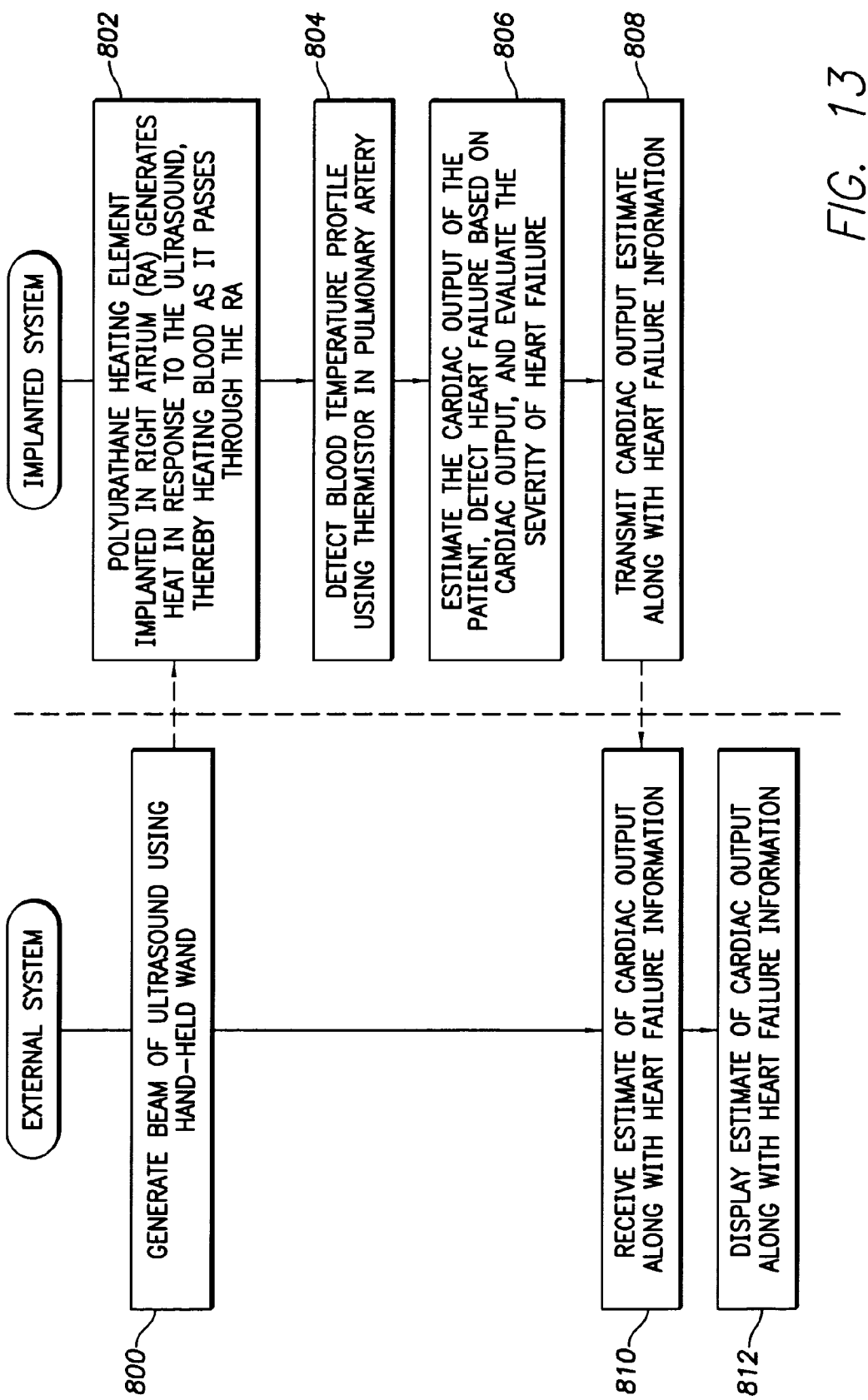
FIG. 13 is a flowchart illustrating steps of a first exemplary implementation of the general method of FIG. 12 wherein an external device calculates cardiac output based on thermal dilution information transmitted from the implanted device.

Referring briefly to FIG. 13, beginning at step 800, the external system transmits power via ultrasound using the hand-held wand, which causes, at step 802, the ultrasound-responsive heating element implanted in the right atrium to generate heat thus heating blood as it passes the heating element. At step 804, the implanted system detects the resulting thermal dilution blood temperature profile using the thermistor implanted in the pulmonary artery and, at step 806, estimates cardiac output, detects the onset of heart failure, and evaluates its severity, using techniques already described. At step 808, this information is transmitted via telemetry to the external system, which receives the data at step 810 for display at step 812. Although not shown in FIG. 13, the implanted system may also exploit the cardiac output estimate and heart failure evaluation to directly control therapy.

Figure 14:
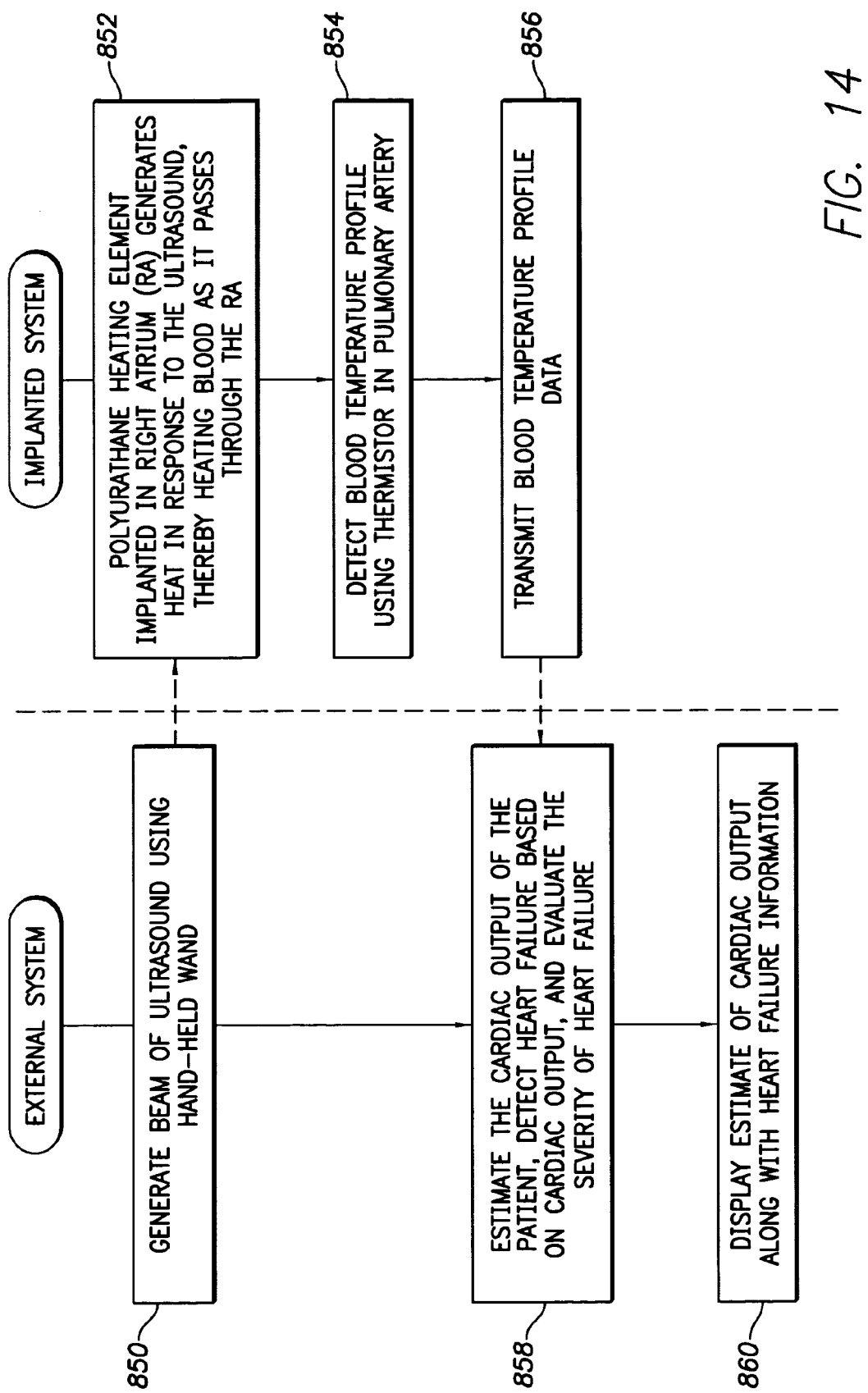
FIG. 14 is a flowchart illustrating steps of a second exemplary implementation of the general method of FIG. 12 wherein the implanted device itself calculates cardiac output based on thermal dilution.

Turning now to FIG. 14, at step 850, the external system likewise transmits power via ultrasound using the hand-held wand, which at step 852 causes the heating element to generate heat thus heating blood as it passes. At step 854, the implanted system detects the resulting thermal dilution blood temperature profile and, at step 856, transmits the profile to the external system. At step 858, the external system then estimates cardiac output, detects the onset of heart failure, and evaluates its severity, using techniques already described. At step 860, the estimated cardiac output is displayed along with information pertaining to the detection and evaluation of heart failure, if any, occurring within the patient. Although not shown in FIG. 14, the external system may transmit its cardiac output estimate and its evaluation of heart failure back to the implanted system, which may then use that information to directly control therapy.

For the sake of completeness, an exemplary pacer/ICD will now be described, which includes components for performing the above-described cardiac output estimation and heart failure evaluation techniques based on power delivered via ultrasound. Many of the components are identical or similar to those of the electromagnetic induction-based system of FIGS. 8-9 and hence only pertinent differences will be described.

Exemplary Implantable System Using Ultrasound-Responsive Heating Element

FIG. 15 illustrates pacer/ICD 710, which includes an ultrasound-responsive heating element 722 for use in heating blood in response to a beam of ultrasound as the blood passes through the right atrium. An optional ultrasound transducer 723 may also be provided for use in measuring the amount of power received via ultrasound by the heating element. In the example of FIG. 15, the heating element is shown mounted along right ventricular lead 330 within the right atrium. Note that the heating element is a passive element and does not receive or transmit signals to/from the pacer/ICD along the lead, (with the possible exception of signals from the ultrasound transducer 723, if provided.) Accordingly, the heating element need not be mounted to a lead. Instead, it could be implanted as a stand-alone component within the right atrium. Mounting of the heating element to a pacing/sensing lead (such as lead 330) is preferred because a lead provides a simple method for positioning the heating element within the right atrium. All other leads and electrodes may be the same as in the system of FIG. 8, described above, with the exception that no power delivery coil (such as coil 18 of FIG. 8) is employed in the embodiment of FIG. 15.

The ideal shape for an ultrasound-responsive heating element is a sphere, because a sphere presents a uniform effective cross-sectional area to the ultrasound beam regardless of the orientation of the element relative to the beam. This removes a source of variability in the amount of power received by the element. However, a single sphere on a lead large enough to serve as a heating element would likely preclude transvenous delivery of the lead. A series of small spheres mounted close together such that they all rest within the right atrium would address this issue. A cylindrical heating element is more practical from the standpoints of manufacturability and deliverability. However any angle between the axis of the cylinder and the tangent to the incident ultrasound wavefronts reduces the effective cross sectional area, and thus reduces the power absorbed. In this case, a cylindrical ultrasound transducer 723 for measuring incident power as discussed above, sharing the same axis with the cylindrical heating element, would be appropriate. The voltage signal from the transducer would be related both to the incident power and to the orientation of the transducer (and therefore the heating element) in the ultrasound beam.

Figure 16:
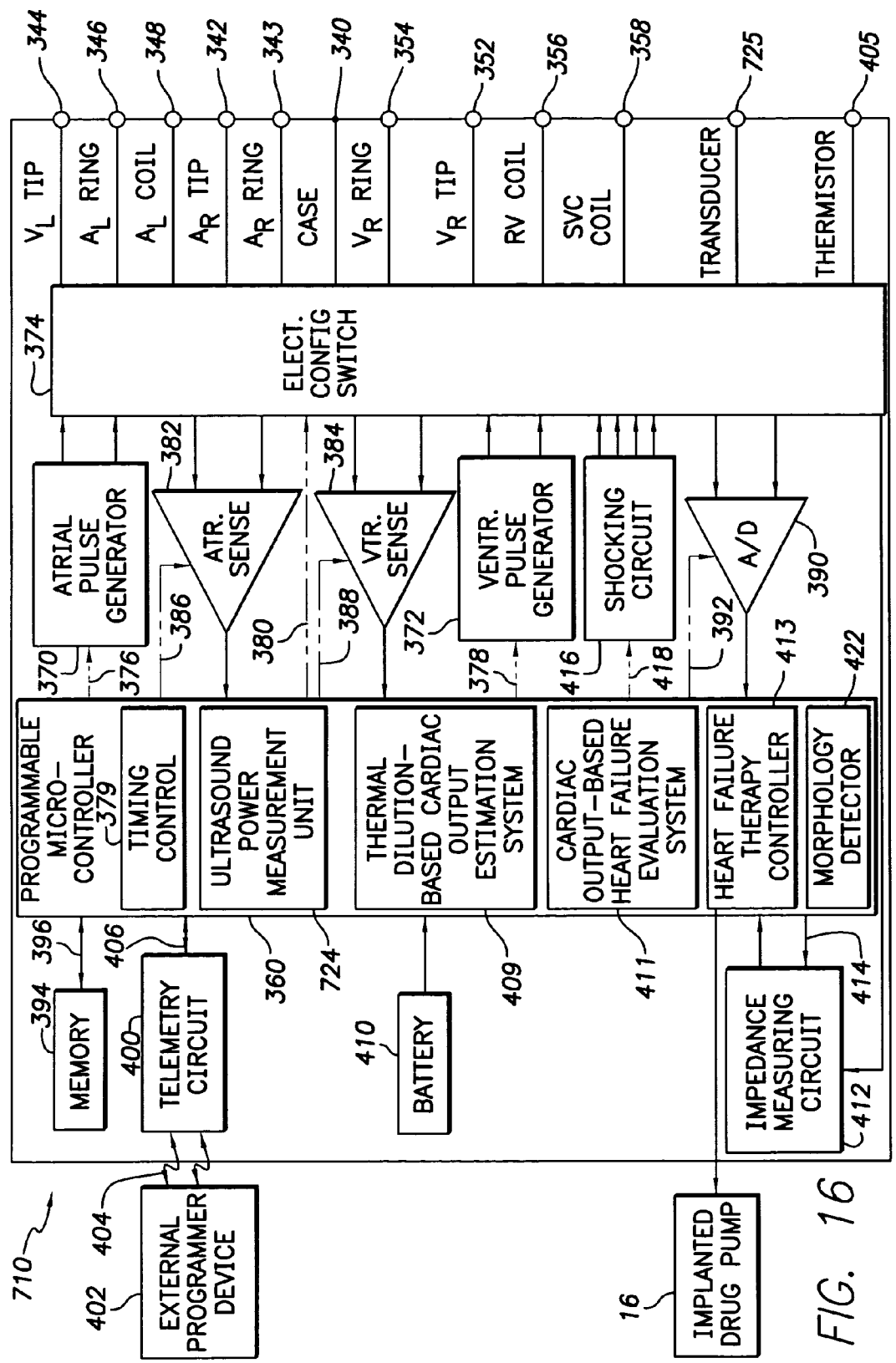
FIG. 16 is a functional block diagram of the pacer/ICD of FIG. 15, illustrating basic circuit elements that provide cardioversion, defibrillation and/or pacing stimulation in the heart and particularly illustrating components for detecting cardiac output and heart failure using the ultrasound thermal dilution-based techniques of FIGS. 12-14.

A simplified block diagram of internal components of pacer/ICD 710 is shown in FIG. 16. All components may be the same as the pacer/ICD of FIG. 9, with the exception that no power regulator (such as regulator 335 of FIG. 9) is required and no power regulation controller (such as controller 407 of FIG. 9) is required. An ultrasound power measurement unit 724 to measure power is provided, if a transducer 723 for measuring incident ultrasound power is included as part of the heating element as described above. An additional terminal 725 for receiving signals from the transducer is also provided. Data identifying the amount of power delivered via ultrasound to the heating element is sent via telemetry to the microcontroller so that it can be used as the Power$_{in}$ value in the estimation of cardiac output (FIG. 3) by thermal dilution-based cardiac output estimation system 409. Alternatively, the thermal dilution profile data may be transmitted via telemetry circuit 400 to the external system so that the external system can instead calculate cardiac output. If so, then the thermal dilution-based cardiac output estimation system need not be provided in the pacer/ICD. As before, a cardiac output-based heart failure evaluation system 411 may be provided to evaluate heart failure, if any, within the patient based on cardiac output using techniques described above in connection with FIG. 4. Alternatively, this evaluation may be performed by the external system and, if so, then a cardiac output-based heart failure evaluation system need no be provided in the pacer/ICD. The microcontroller is also shown to include a heart failure therapy controller 413, which controls the delivery of therapy in response to heart failure using techniques summarized in FIG. 5. This includes controlling a drug pump, if so equipped, to deliver any appropriate medications. Note that if the pacer/ICD does not include internal components for detecting heart failure, then the heart failure therapy controller operates based on any heart failure data received from the external system via telemetry circuit 400.

Exemplary External Ultrasound Delivery System/Programmer

Figure 17:
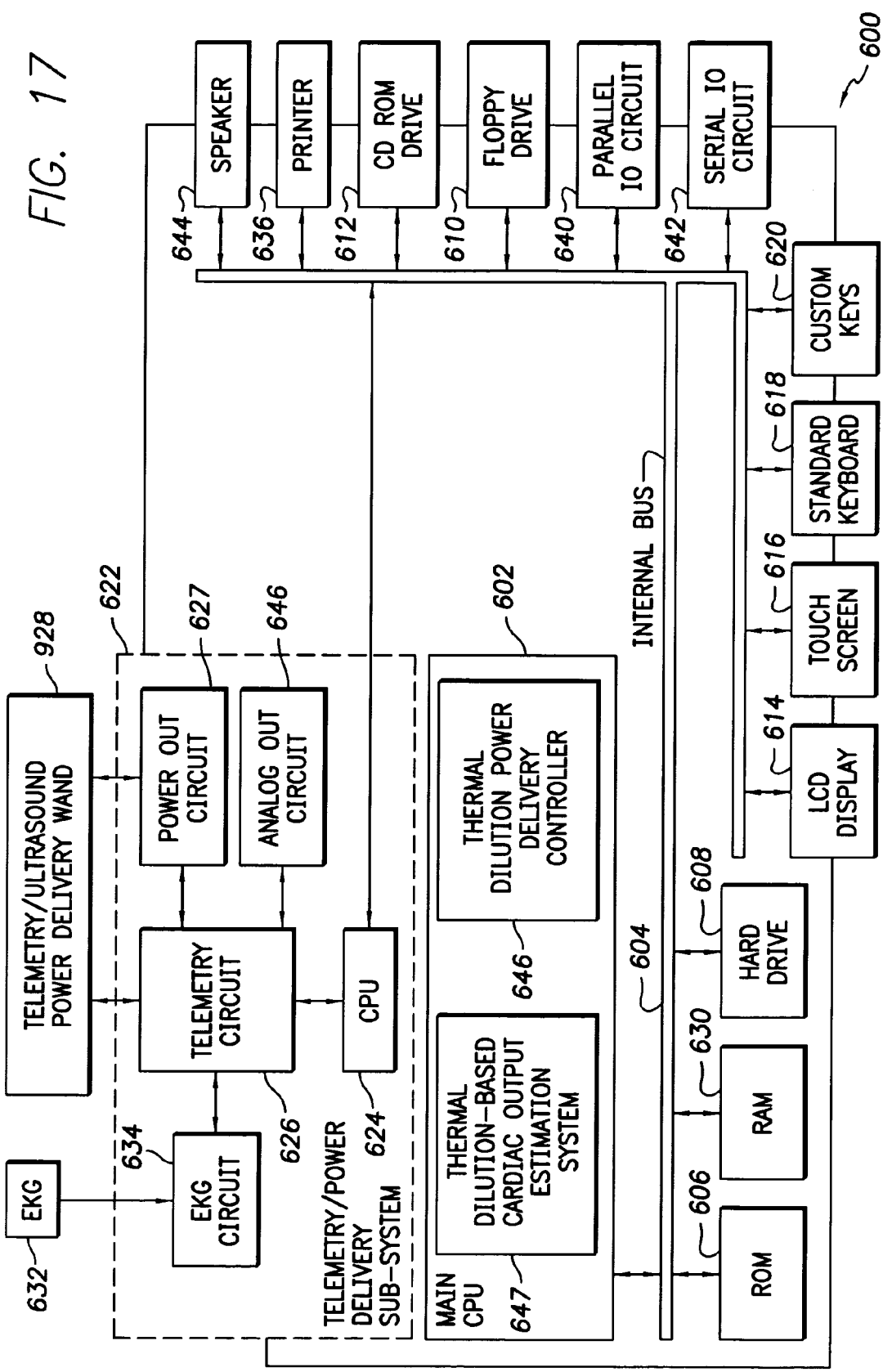
FIG. 17 is a functional block diagram of an external programmer/bedside monitoring device for delivering power to the implanted system of FIGS. 15-16 via ultrasound and for calculating and/or displaying cardiac output values calculated using the techniques of FIGS. 12-14.

FIG. 17 illustrates pertinent components of an external programmer for use in delivering power via ultrasound to the heating element of the implanted system for thermal dilution analysis. All components may be the same as the programmer of FIG. 10, with the exception that an ultrasound power delivery wand 928 is provided instead of an electromagnetic induction wand. Exemplary techniques for generating ultrasound for medical applications are set forth in the following patents and patent applications: U.S. Patent Application 2003/0149380 of Fujimoto et al., entitled "Ultrasound Treatment Apparatus"; U.S. Pat. No. 5,394,875 to Lewis et al., entitled "Automatic Ultrasonic Localization of Targets Implanted in a Portion of the Anatomy"; U.S. Patent Application: 2003/0216721 of Diederich et al, entitled "System and Method Providing Directional Ultrasound Therapy to Skeletal Joints"; and U.S. Patent Application: 2003/0018255 of Martin et al., entitled "Method and Apparatus for Medical Procedures using High-Intensity Focused Ultrasound."

If the implanted device is not equipped to estimate cardiac output based on thermal dilution data, then the device transmits the data to the external programmer, which receives the data via wand 928. The programmed then uses a thermal dilution-based cardiac output estimation system 647 to estimate cardiac output based on the data, using the techniques of FIG. 3. Note that, for the purposes of power delivery for thermal dilution analysis, a full device programmer need not be used. Rather, it is sufficient to provide an external device capable of delivering power via ultrasound to the implanted heating element. A full function programmer has been illustrated for the sake of completeness.

What have been described are techniques and systems for estimating cardiac output using thermal dilution and for detecting and evaluation heart failure. Principles of the invention may be exploiting using other implantable systems or in accordance with other techniques. Indeed, general principles invention may be exploited with systems not incorporating pacemakers or ICDs but instead incorporating other implantable medical devices. In addition, whereas an example has been described wherein the heating coil/elements in the RA and the thermistor is in the pulmonary artery, this need not be the case and other appropriate locations may instead be selected. As can be appreciated, a wide variety of specific implementations may be developed consistent with the principles of the invention and no attempt is made herein to describe or enumerate all such possible implementations. Thus, while the invention has been described with reference to particular embodiments, modifications can be made thereto without departing from the spirit and scope of the invention. Note also that the term "including" as used herein is intended to be inclusive, i.e. "including but not limited to."

What is claimed is:

1. An implantable system for use within a patient, the system comprising an implantable medical device adapted to be implanted within the patient, the system further comprising:
- a heating element capable of generating heat in response to ultrasound, with the heating element configured for implant in proximity to blood being pumped within the patient for heating a quantity of blood in response to ultrasound generated by a source configured to be positioned external to the patient;
- a blood temperature sensor configured for implant downstream from the heating element for detecting a temperature profile of blood heated by the heating element; and
- a device operative to route signals representative of the blood temperature profile to the implantable medical device.

2. The system of claim 1 wherein the heating element includes an acoustic absorber absorptive at ultrasonic frequencies.

3. The system of claim 2 wherein the acoustic absorber includes a polyurethane material.

4. The system of claim 3 wherein the polyurethane material is formed of RP-6401 polyurethane.

5. The system of claim 1 wherein the heating element is adapted to be positioned within a right atrium of the patient and wherein the temperature sensor is adapted to be implanted in a pulmonary artery of the patient.

6. The system of claim 1 further including an ultrasound transducer mounted to the heating element and operative to measure incident power.

7. The system of claim 1 wherein the device operative to route signals representative of the blood temperature profile to the implantable medical device is a lead implanted within the heart of the patient.

8. A method for measuring cardiac output within a patient having an implantable medical system equipped with a blood temperature sensor, a heating element capable of generating heat in response to ultrasound, and a cardiac output detection system, the method comprising:
- directing a beam of ultrasound generated by a source configured to be positioned external to the patient onto the heating element causing the heating element to generate heat so that blood adjacent the heating element is heated;
- measuring a resulting temperature profile of the blood using the temperature sensor at a location downstream from the heating element;
- estimating the cardiac output of the patient using the cardiac output detection system based, in part, on the resulting temperature profile; and
- employing the estimated cardiac output to control at least one system function.

9. The method of claim 7 wherein the heating element is adapted to be positioned within a right atrium of the patient and wherein directing a beam of ultrasound onto the heating element is performed by directing a beam of ultrasound toward the right atrium.

10. The method of claim 7 wherein the temperature sensor is adapted to be implanted in a pulmonary artery of the patient and wherein measuring the resulting temperature profile of the blood using the temperature sensor is performed to measure the temperature profile of blood passing within the pulmonary artery.

11. The method of claim 7 further comprising tracking changes in the cardiac output of the patient over time using the cardiac output detection system to detect the onset of a selected medical condition within the patient based on the changes in cardiac output over time.

12. The method of claim 11 further comprising detecting the onset of a selected medical condition within the patient based on changes in cardiac output over time.

13. The method of claim 12 further comprising tracking changes, if any, in the severity of the medical condition within the patient using the cardiac output detection system based on any changes over time in the cardiac output of the patient to detect congestive heart failure (CHF).

14. The method of claim 11 wherein the system is equipped to deliver therapy to the patient and wherein the method further comprises controlling the system to deliver therapy in response to the medical condition.

15. The method of claim 14 wherein the system is equipped with a cardiac resynchronization therapy (CRT) system and wherein the therapy includes CRT.

16. The method of claim 15 wherein the system is equipped with an implantable drug pump and wherein delivering therapy includes delivering selected medications to the patient using the drug pump.

17. The method of claim 11 wherein the system is equipped with a warning device and wherein the method further comprises generating a warning signal using the warning device in response to the medical condition.

18. The method of claim 11 wherein tracking changes in the cardiac output of the patient to detect the onset of the medical condition is performed by an external device based on signals received from the implanted device.

* * * * *

UNITED STATES PATENT AND TRADEMARK OFFICE
CERTIFICATE OF CORRECTION

PATENT NO.         : 7,632,235 B1                                         Page 1 of 1
APPLICATION NO.    : 11/099888
DATED              : December 15, 2009
INVENTOR(S)        : Karicherla et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1227 days.

Signed and Sealed this

Second Day of November, 2010

David J. Kappos
*Director of the United States Patent and Trademark Office*